United States Patent
Ushioda et al.

(10) Patent No.: US 8,673,915 B2
(45) Date of Patent: Mar. 18, 2014

(54) P 2×4 RECEPTOR ANTAGONIST

(75) Inventors: Masatoshi Ushioda, Misato (JP); Shogo Sakuma, Misato (JP); Atsushi Tendo, Misato (JP); Toshiyasu Imai, Misato (JP); Kazuhide Inoue, Fukuoka (JP)

(73) Assignee: Nippon Chemiphar Co., Ltd., Tokyo (JP)

( * ) Notice: Subject to any disclaimer, the term of this patent is extended or adjusted under 35 U.S.C. 154(b) by 0 days.

(21) Appl. No.: 13/811,714

(22) PCT Filed: Jul. 27, 2011

(86) PCT No.: PCT/JP2011/067027
§ 371 (c)(1),
(2), (4) Date: Mar. 29, 2013

(87) PCT Pub. No.: WO2012/014910
PCT Pub. Date: Feb. 2, 2012

(65) Prior Publication Data
US 2013/0178625 A1   Jul. 11, 2013

(30) Foreign Application Priority Data

Jul. 29, 2010 (JP) .................................. 2010-170836

(51) Int. Cl.
*A61K 31/498* (2006.01)
*C07D 241/38* (2006.01)

(52) U.S. Cl.
USPC .......................................... 514/250; 544/344

(58) Field of Classification Search
USPC .......................................... 544/344; 514/250
See application file for complete search history.

(56) References Cited

U.S. PATENT DOCUMENTS

2003/0114422 A1*  6/2003  Bigge et al. ................... 514/80
2005/0074819 A1   4/2005  Inoue et al.

* cited by examiner

*Primary Examiner* — Kristin Vajda
(74) *Attorney, Agent, or Firm* — Nixon Peabody LLP; Jeffrey L. Costellia

(57) ABSTRACT

A compound having the following formula (II) or a pharmacologically acceptable salt thereof is used as a $P2X_4$ receptor antagonist:

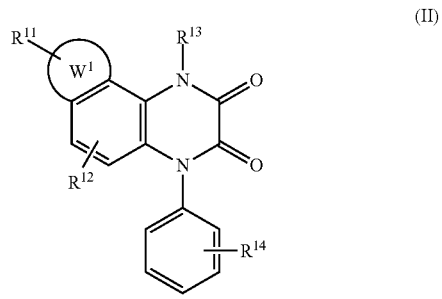

(II)

wherein each of $R^{11}$ and $R^{12}$ is hydrogen, $C_{1-8}$ alkyl or the like;
$R^{13}$ is hydrogen, $C_{1-8}$ alkyl or the like;
$R^{14}$ is hydrogen, $C_{1-8}$ alkyl, $C_{1-8}$ alkoxy, $C_{1-8}$ alkyl having 1-3 halogens, $C_{1-8}$ hydroxyalkyl, halogen, hydroxyl, nitro, cyano, amino, $C_{1-8}$ alkylamino, benzenesulfonylamino optionally having a substituent, a heterocyclic group optionally having a substituent or the like; and
the condensed ring consisting of $W^1$ and the neighboring benzene ring is naphthalene, tetrahydronaphthalene, or indan ring.

21 Claims, No Drawings

P 2×4 RECEPTOR ANTAGONIST

FIELD OF THE INVENTION

The present invention relates to a diazepine derivative showing P2X$_4$ receptor antagonism.

BACKGROUND OF THE INVENTION

ATP receptors are basically classified into P2X family of ion-channel type receptors and P2Y family of G protein-coupled receptors. Until now, there are reported, respectively, seven sub-types (P2X$_{1-7}$) and eight sub-types (P2Y$_{1, 2, 4, 6, 11-14}$).

It has been reported that P2X$_4$ receptor (Genebank No. X87763), which is a sub-type of P2X family, is present widely in the central nervous systems (cf. Non-patent documents 1-5).

The mechanism of pathogenesis of intractable pains such as neuropathic pain is unclear. Therefore, if non-steroidal anti-inflammatory drugs (NSAIDs) and morphine are not effective, there is no other pharmacotherapy. In that case, the patient and surrounding people take up a heavy burden in mind and body. The neuropathic pain is caused by injury of peripheral or central nervous systems, for instance, post-surgery pain, cancer, spinal cord injury, herpes zoster, diabetic neuritis, or trigeminal neuralgia.

Recently, Inoue, et al. studied the involvement of P2X receptors in neuropathic pain using dorsal root ganglion neuron-injured animal model, which induces allodynia, and indicated that the nerve-injured pain (particularly, allodynia) is caused via P2X$_4$ receptors on spinal microglia (cf. Non-patent documents 6, 7, and Patent document 1).

Accordingly, compounds that inhibit the action of P2X$_4$ receptors are expected to be employed for preventing or treating nociceptive, inflammatory, and neuropathic pains.

Patent document 2 discloses that benzofuro-1,4-diazepin-2-one derivatives having the below-illustrated formula (A) show P2X$_4$ receptor antagonism:

(A)

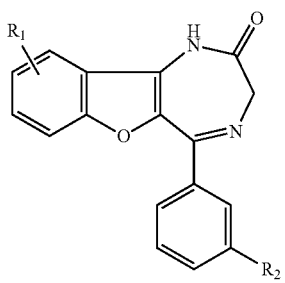

wherein R$_1$ is halogen, and R$_2$ is hydrogen, halogen, nitro, cyano, C(O)—OR$_3$, C(O)—NR$_4$R$_5$, SO$_2$—R$_3$, or SO$_2$—NR$_4$R$_5$, or in which R$^1$ is hydrogen, and R$_2$ is halogen, nitro, cyano, C(O)—OR$_3$, C(O)—NR$_4$R$_5$, SO$_2$—OR$_3$, or SO$_2$—NR$_4$R$_5$.

Non-patent document 8 discloses that Paroxetine known as an antidepressant also shows P2X$_4$ receptor antagonism.

The present inventors have found that naphtho[1,2-e]-1,4-diazepin-2-one derivatives having the below-illustrated formula (B) showing P2X$_4$ receptor antagonism, and filed the Patent document 3.

(B)

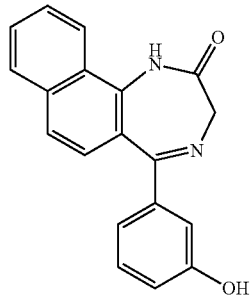

Patent document 4 discloses a naphtho[1,2-b]-1,4-diazepin-4-one derivative represented by the following formula (C).

(C)

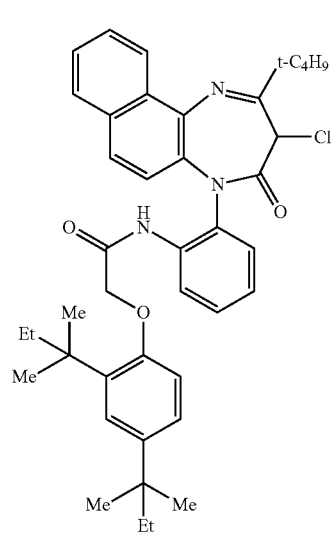

Patent document 4 describes that the compound represented by the formula (C) can be used as photographic couplers. Patent document 4, however, is silent with respect to the relation between the compound and the P2X$_4$ receptor antagonism.

Patent document 5 describes the quinoxaline compound represented by the formula (D).

(D)

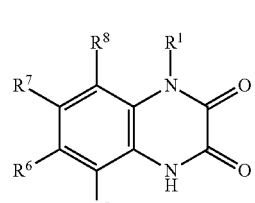

In the formula (D), R$^1$ can be an aryl group, and R$^5$ and R$^6$ can be combined together to form an aromatic ring. Patent document 5, however, is silent with respect to an example of a quinoxaline compound wherein R$^1$ is an aryl group. Patent document 5 describes that the quinoxaline compound represented by the formula (D) has a quisqualate receptor antagonism. Patent document 5, however, is silent with respect to the relation between the compound and the P2X$_4$ receptor antagonism.

PRIOR ART DOCUMENTS

Patent Documents

Patent document 1: United States patent publication No. 20050074819
Patent document 2: WO 2004/085440
Patent document 3: WO 2008/023847
Patent document 4: Japanese Patent Publication No. 2 (1990)-304437
Patent document 5: Japanese Patent Publication No. 1 (1989)-153680

Non-Patent Documents

Non-patent document 1: Buell, et al. (1996) EMBO J. 15: 55-62
Non-patent document 2: Seguela, et al. (1996) J. Neurosci. 16: 448-455
Non-patent document 3: Bo, et al. (1995) FEBS Lett. 375: 129-133
Non-patent document 4: Soto, et al. (1996) Proc. Natl. Acad. Sci. USA 93: 3684-3788
Non-patent document 5: Wang, et al. (1996) Biochem. Res. Commun. 220: 196-202
Non-patent document 6: M. Tsuda, et al. (2003) Nature, 424, 778-783
Non-patent document 7: Jeffrey A. M. Coull, et al. (2005) Nature, 438, 1017-1021
Non-patent document 8: Paper Abstract of Lecture Program P3-N-114, The 49th Annual Meeting of Japanese Society for Neurochemistry (2006)

SUMMARY OF THE INVENTION

Problems to be Solved by the Invention

It is the object of the present invention to provide a compound represented by the formula (I) or (II), which shows P2X$_4$ receptor antagonism.

Means for Solving the Problems

The present invention relates to a compound having the following formula (I) or a pharmacologically acceptable salt thereof:

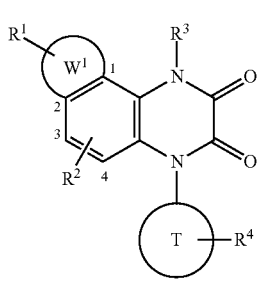
(I)

wherein each of $R^1$ and $R^2$ independently is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, an aralkyl group consisting of a $C_{6-10}$ aryl moiety and a $C_{1-3}$ alkylene moiety, a halogen atom, hydroxyl, nitro, cyano, amino, a $C_{1-8}$ alkylamino group, a $C_{2-8}$ dialkylamino group, a $C_{2-8}$ acylamino group, a $C_{2-8}$ acylamino group having one to three halogen atoms, a $C_{1-8}$ alkylsulfonylamino group, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, or sulfamoyl;

$R^3$ is hydrogen, a $C_{1-8}$ alkyl group, a $C_{2-8}$ alkenyl group, a $C_{1-8}$ alkyl group having one to three halogen atoms, or an aralkyl group consisting of a $C_{6-10}$ aryl moiety and a $C_{1-3}$ alkylene moiety;

$R^4$ is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, an aralkyl group consisting of a $C_{6-10}$ aryl moiety and a $C_{1-3}$ alkylene moiety, a $C_{1-8}$ alkyl group having hydroxyl, a halogen atom, hydroxyl, nitro, cyano, amino, a $C_{1-8}$ alkylamino group, a $C_{1-5}$ alkylamino group having one to five halogen atoms, a $C_{2-8}$ dialkylamino group, a $C_{2-8}$ acylamino group, a $C_{2-8}$ acylamino group having one to three halogen atoms, a $C_{1-8}$ alkylsulfonylamino group, benzenesulfonylamino optionally having one or more substituents, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, sulfamoyl, phenyl optionally having one or more substituents, or a heterocyclic group optionally having one or more substituents;

the ring shown below is a five-membered to eight-membered ring optionally comprising one or more heteroatoms selected from N, S, and O as the members of the ring, and being condensed with the benzene ring at the positions of 1 and 2 of the benzene ring; and

the ring shown below is an aromatic ring selected from the group consisting of benzene ring, naphthalene ring, pyridine ring, pyrimidine ring, quinoline ring, indole ring, indoline ring, benzimidazole ring, indazole ring, benzisoxazole ring, and benzotriazole ring.

The invention also relates to a compound having the following formula (II) or a pharmacologically acceptable salt thereof:

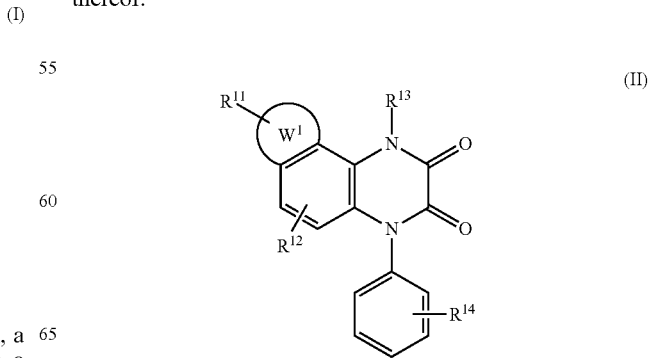
(II)

wherein each of $R^{11}$ and $R^{12}$ independently is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, an aralkyl group consisting of a $C_{6-10}$ aryl moiety and a $C_{1-3}$ alkylene moiety, a halogen atom, hydroxyl, nitro, cyano, amino, a $C_{1-8}$ alkylamino group, a $C_{2-8}$ dialkylamino group, a $C_{2-8}$ acylamino group, a $C_{2-8}$ acylamino group having one to three halogen atoms, a $C_{1-8}$ alkylsulfonylamino group, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, or sulfamoyl;

$R^{13}$ is hydrogen, a $C_{1-8}$ alkyl group, a $C_{2-8}$ alkenyl group, a $C_{1-8}$ alkyl group having one to three halogen atoms, or an aralkyl group consisting of a $C_{6-10}$ aryl moiety and a $C_{1-3}$ alkylene moiety;

$R^{14}$ is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, an aralkyl group consisting of a $C_{6-10}$ aryl moiety and a $C_{1-3}$ alkylene moiety, a $C_{1-8}$ alkyl group having hydroxyl, a halogen atom, hydroxyl, nitro, cyano, amino, a $C_{1-8}$ alkylamino group, a $C_{1-5}$ alkylamino group having one to five halogen atoms, a $C_{2-8}$ dialkylamino group, a $C_{2-8}$ acylamino group, a $C_{2-8}$ acylamino group having one to three halogen atoms, a $C_{1-8}$ alkylsulfonylamino group, benzenesulfonylamino optionally having one or more substituents, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, sulfamoyl, phenyl optionally having one or more substituents, or a heterocyclic group optionally having one or more substituents; and the ring shown below is naphthalene ring, tetrahydronaphthalene ring, or indan ring.

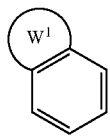

The invention also relates to a $P2X_4$ receptor antagonist containing a compound represented by the formula (I) or (II), or its pharmacologically acceptable salt as an active ingredient.

The invention further relates to a preventive or therapeutic agent for neuropathic pains containing a compound represented by the formula (I) or (II), or its pharmacologically acceptable salt as an active ingredient.

THE EMBODIMENTS OF THE INVENTION

The present invention is described below in more detail.

In the compound of the present invention represented by the formula (I), the alkyl group having 1 to 8 carbon atoms for $R^1$, $R^2$, $R^3$, and $R^4$ can be methyl, ethyl, propyl, isopropyl, butyl, isobutyl, t-butyl, pentyl, or hexyl.

The alkenyl group having 2 to 8 carbon atoms for $R^1$, $R^2$, $R^3$, and $R^4$ can be allyl.

The alkyl group having 1 to 8 carbon atoms substituted with one to three halogen atoms for $R^1$, $R^2$, $R^3$, and $R^4$ can be methyl, ethyl, propyl, isopropyl, butyl, or t-butyl substituted with one to three halogen atoms such as 1 to 3 fluoro, chloro, or bromo atoms, and preferably is trifluoromethyl, chloromethyl, 2-chloroethyl, 2-bromoethyl, or 2-fluoroethyl.

The aralkyl group consisting of an aryl moiety having 6 to 10 carbon atoms and an alkylene moiety having 1 to 3 carbon atoms for $R^1$, $R^2$, $R^3$, and $R^4$ can be benzyl.

The alkoxy group having 1 to 8 carbon atoms for $R^1$, $R^2$, and $R^4$ can be methoxy, ethoxy, propoxy, isopropoxy, butoxy, isobutoxy, t-butoxy, pentyloxy, or hexyloxy.

The alkoxy group having 1 to 8 carbon atoms substituted with one to three halogen atoms for $R^1$, $R^2$, and $R^4$ can be methoxy, ethoxy, propoxy, isopropoxy, butoxy, isobutoxy, or t-butoxy substituted with one to three halogen atoms such as 1 to 3 fluoro, chloro, or bromo atoms, and preferably include trifluoromethoxy, chloromethoxy, 2-chloroethoxy, 2-bromoethoxy, or 2-fluoroethoxy.

The halogen atom for $R^1$, $R^2$, and $R^4$ can be fluoro, chloro, or bromo atom.

The alkylamino group having 1 to 8 carbon atoms for $R^1$, $R^2$, and $R^4$ can be methylamino or ethylamino.

The alkylamino group having 1 to 5 carbon atoms substituted with 1 to 5 halogen atoms for $R^4$ can be 2,2,2-trifluoroethylamino.

The dialkylamino group having 2 to 8 carbon atoms for $R^1$, $R^2$, and $R^4$ can be dimethylamino or diethylamino.

The acylamino group having 2 to 8 carbon atoms for $R^1$, $R^2$, and $R^4$ can be acetylamino. It can also be benzoylamino optionally having one or more substituents (selected from the group consisting of an alkyl group having 1 to 8 carbon atoms, an alkoxy group having 1 to 8 carbon atoms, an alkyl group having 1 to 8 carbon atoms substituted with one to three halogen atoms, an alkoxy group having 1 to 8 carbon atoms substituted with one to three halogen atoms, and a halogen atom).

The acylamino group having 2 to 8 carbon atoms substituted with one to three halogen atoms for $R^1$, $R^2$, and $R^4$ can be trifluoromethylcarbonylamino.

The alkylsulfonylamino group having 1 to 8 carbon atoms for $R^1$, $R^2$, and $R^4$ can be methylsulfonylamino.

The acyl group having 2 to 8 carbon atoms for $R^1$, $R^2$, and $R^4$ can be acetyl.

The alkoxycarbonyl group comprising an alkoxy moiety having 1 to 8 carbon atoms for $R^1$, $R^2$, and $R^4$ can be methoxycarbonyl or ethoxycarbonyl.

The alkylthio group having 1 to 8 carbon atoms for $R^1$, $R^2$, and $R^4$ can be methylthio.

The alkylsulfinyl group having 1 to 8 carbon atoms for $R^1$, $R^2$, and $R^4$ can be methylsulfinyl.

The alkylsulfonyl group having 1 to 8 carbon atoms for $R^1$, $R^2$, and $R^4$ can be methylsulfonyl.

The alkyl group having 1 to 8 carbon atoms substituted with hydroxyl for $R^4$ can be hydroxymethyl.

With respect to the benzenesulfonylamino optionally having one or more substituents for $R^4$, the substituent preferably is selected from the group consisting of an alkyl group having 1 to 8 carbon atoms (such as methyl, ethyl), an alkoxy group having 1 to 8 carbon atoms (such as methoxy, ethoxy), a halogen atom (such as fluoro atom, chloro atom), and nitro. It preferably is o-nitrobenzenesulfonylamino.

With respect to the phenyl optionally having one or more substituents for $R^4$, the substituent preferably is an alkyl group having 1 to 8 carbon atoms (such as methyl, ethyl), an alkyl group having 1 to 8 carbon atoms substituted with one to three halogen atoms (such as trifluoromethyl), a halogen atom (such as fluoro atom), or cyano.

The heterocyclic group optionally having one or more substituents for $R^4$ preferably is tetrazolyl, triazolyl, pyridyl, imidazolyl, oxazolyl, or triazolyl. The heterocyclic group can also be oxadiazolyl.

With respect to the heterocyclic group optionally having one or more substituents for $R^4$, the substituent preferably is an alkyl group having 1 to 8 carbon atoms (such as methyl, ethyl), an alkyl group having 1 to 8 carbon atoms substituted with one to three halogen atoms (such as trifluoromethyl), a halogen atom (such as fluoro atom), cyano, or oxo.

$R^1$, $R^2$, and $R^4$ in the formula (I) can be the same or different two or more substituents attached to the rings to which $R^1$, $R^2$, and $R^4$ are attached.

Examples of $R^{11}$, $R^{12}$, $R^{13}$, and $R^{14}$ in the formula (II) are the same as the examples of the alkyl group having 1 to 8 carbon atoms, the alkenyl group having 2 to 8 carbon atoms, the alkoxy group having 1 to 8 carbon atoms, the alkyl group having 1 to 8 carbon atoms substituted with one to three halogen atoms, the alkoxy group having 1 to 8 carbon atoms substituted with one to three halogen atoms, the aralkyl group consisting of an aryl moiety having 6 to 10 carbon atoms and an alkylene moiety having 1 to 3 carbon atoms, the alkyl group having 1 to 8 carbon atoms substituted with hydroxyl, the halogen atom, the alkylamino group having 1 to 8 carbon atoms, the alkylamino group having 1 to 5 carbon atoms substituted with 1 to 5 halogen atoms, the dialkylamino group having 2 to 8 carbon atoms, the acylamino group having 2 to 8 carbon atoms, the acylamino group having 2 to 8 carbon atoms substituted with one to three halogen atoms, the alkylsulfonylamino group having 1 to 8 carbon atoms, the benzenesulfonylamino optionally having one or more substituents, the acyl group having 2 to 8 carbon atoms, the alkoxycarbonyl group comprising an alkoxy moiety having 1 to 8 carbon atoms, the alkylthio group having 1 to 8 carbon atoms, the alkylsulfinyl group having 1 to 8 carbon atoms, the alkylsulfonyl group having 1 to 8 carbon atoms, the phenyl optionally having one or more substituents, and the heterocyclic group optionally having one or more substituents for $R^1$, $R^2$, $R^3$, and $R^4$ in the formula (I).

With respect to the heterocyclic group optionally having one or more substituents for $R^{14}$ in the formula (II), examples of the substituents are the same as the examples of the alkyl group having 1 to 8 carbon atoms, the alkoxy group having 1 to 8 carbon atoms, the alkyl group having 1 to 8 carbon atoms substituted with one to three halogen atoms, the alkoxy group having 1 to 8 carbon atoms substituted with one to three halogen atoms, the halogen atoms, the alkylamino group having 1 to 8 carbon atoms, and the dialkylamino group having 2 to 8 carbon atoms for $R^2$ to $R^4$ in the formula (I).

$R^{11}$, $R^{12}$, and $R^{14}$ in the formula (II) can be the same or different two or more substituents attached to the rings to which $R^{11}$, $R^{12}$, and $R^{14}$ are attached.

The compound of the present invention of the formula (I) preferably is the following compound.

(1) A compound having the formula (I) or a pharmacologically acceptable salt thereof, wherein each of $R^1$ and $R^2$ independently is hydrogen, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, or amino.

(2) A compound having the formula (I), a compound of (1), or a pharmacologically acceptable salt thereof, wherein $R^3$ is hydrogen or a $C_{1-8}$ alkyl group.

(3) A compound having the formula (I), a compound of (1) or (2), or a pharmacologically acceptable salt thereof, wherein $R^4$ is hydrogen, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a $C_{1-8}$ alkyl group having hydroxyl, a halogen atom, hydroxyl, cyano, amino, a $C_{1-8}$ alkylamino group, a $C_{2-8}$ dialkylamino group, a $C_{1-8}$ alkylsulfonylamino group, benzenesulfonylamino optionally having one or more substituents, phenyl optionally having one or more substituents, or a heterocyclic group optionally having one or more substituents.

(4) A compound having the formula (I), a compound of (1) or (2), or a pharmacologically acceptable salt thereof, wherein $R^4$ is a heterocyclic group optionally having one or more substituents, said heterocyclic group being tetrazolyl, triazolyl, pyridyl, imidazolyl, oxazolyl, or triazolyl, and said substituents being selected from the group consisting of a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, and a $C_{2-8}$ dialkylamino group.

(5) A compound having the formula (I), a compound of (1) or (2), or a pharmacologically acceptable salt thereof, wherein $R^4$ is hydrogen, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, cyano, amino, a $C_{1-8}$ alkylamino group, a $C_{2-8}$ dialkylamino group, or benzenesulfonylamino optionally having one or more substituents, said substituents being selected from the group consisting of a $C_{1-8}$ alkyl group, a $C_{1-8}$ alkoxy group, a halogen atom, and nitro.

(6) A compound having the formula (I), a compound of one of (1) to (5), or a pharmacologically acceptable salt thereof, wherein the ring shown below is naphthalene ring, tetrahydronaphthalene ring, or indan ring.

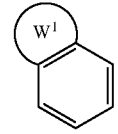

(7) A compound having the formula (I), a compound of one of (1) to (6), or a pharmacologically acceptable salt thereof, wherein the ring shown below is benzene ring or indole ring.

The compound of the present invention of the formula (II) preferably is the following compound.

(8) A compound having the formula (II) or a pharmacologically acceptable salt thereof, wherein each of $R^{11}$ and $R^{12}$ independently is hydrogen, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, or amino.

(9) A compound having the formula (II), a compound of (8), or a pharmacologically acceptable salt thereof, wherein $R^{13}$ is hydrogen or a $C_{1-8}$ alkyl group.

(10) A compound having the formula (II), a compound of (8) or (9), or a pharmacologically acceptable salt thereof, wherein $R^{14}$ is hydrogen, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a $C_{1-8}$ alkyl group having hydroxyl, a halogen atom, hydroxyl, cyano, amino, a $C_{1-8}$ alkylamino group, a $C_{2-8}$ dialkylamino group, a $C_{1-8}$ alkylsulfonylamino group, benzenesulfonylamino optionally having one or more substituents, phenyl optionally having one or more substituents, or a heterocyclic group optionally having one or more substituents.

(11) A compound having the formula (II), a compound of (8) or (9), or a pharmacologically acceptable salt thereof, wherein $R^{14}$ is a heterocyclic group optionally having one or more substituents, said heterocyclic group being tetrazolyl, triazolyl, pyridyl, imidazolyl, oxazolyl, or triazolyl, and said substituents being selected from the group consisting of a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, and a $C_{2-8}$ dialkylamino group.

(12) A compound having the formula (II), a compound of (8) or (9), or a pharmacologically acceptable salt thereof, wherein $R^{14}$ is hydrogen, a $C_{2-8}$ alkyl group, a $C_{1-8}$ alkoxy group, a $C_{1-8}$ alkyl group having one to three halogen atoms, a $C_{2-8}$ alkoxy group having one to three halogen atoms, a halogen atom, hydroxyl, cyano, amino, a $C_{2-8}$ alkylamino group, a $C_{2-8}$ dialkylamino group, or benzenesulfonylamino optionally having one or more substituents, said substituents being selected from the group consisting of a $C_{2-8}$ alkyl group, a $C_{1-8}$ alkoxy group, a halogen atom, and nitro.

(13) A compound having the formula (II), a compound of one of (8) to (12), or a pharmacologically acceptable salt thereof, wherein the ring shown below is naphthalene ring.

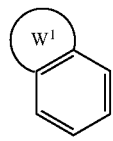

(14) A compound having the formula (II) or a pharmacologically acceptable salt thereof, wherein $R^{11}$, $R^{12}$, $R^{13}$, and the ring shown below are the same as those defined in the formula (II), and $R^{14}$ is $NHSO_2R$, wherein R is an aryl group optionally having one or more substituents or a heterocyclic group optionally having one or more substituents.

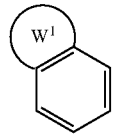

(15) A compound of (14) or a pharmacologically acceptable salt thereof, wherein R is phenyl, naphthyl, quinolyl, pyridyl, or thienyl, each of which optionally has one or more substituents selected from the group consisting of a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, hydroxyl, amino, nitro, and a halogen atom.

The pharmacologically acceptable salts of the compound represented by the formula (I) or (II) include a hydrochloride salt and an alkali metal (e.g., sodium, potassium, lithium) salt.

The compound of the present invention can be a geometrical isomer or an optical isomer such as an optically active substance and racemic modification, each of which is included within the scope of the invention.

The schemes for synthesis of the compound of the invention represented by the formula (I) are shown below.

[Synthesis Method 1]

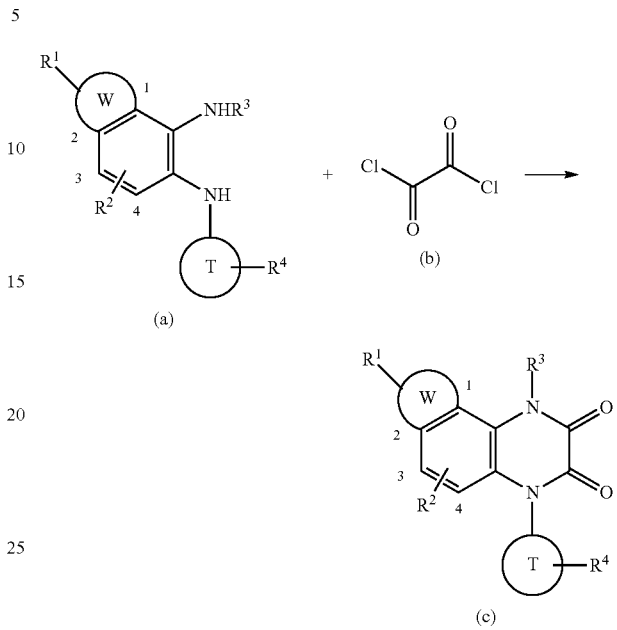

In the above-illustrated formula, $R^1$, $R^2$, $R^3$, $R^4$, and the following rings are defined above.

The compound of the invention represented by the formula (c) can be obtained by subjecting the compound represented by the formula (a) and oxalyl chloride represented by the formula (b) to a ring-closing reaction in the presence of a solvent such as THF.

The compound represented by the formula (a) can be synthesized, for example by the following process.

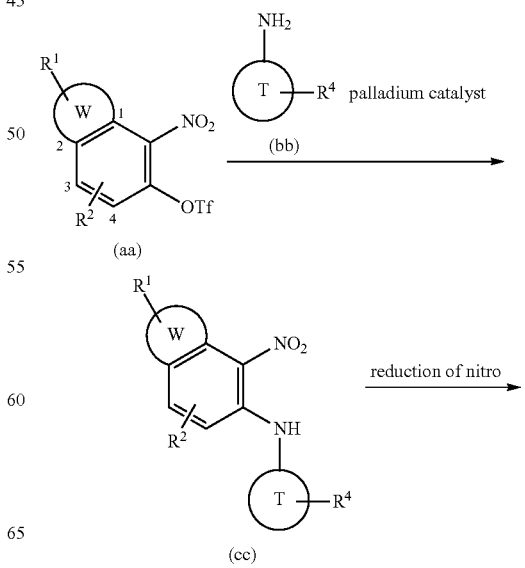

-continued

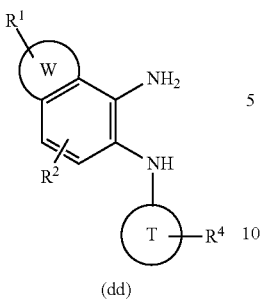

(dd)

In the above-illustrated formula, Tf is trifluoromethane, and $R^1$, $R^2$, $R^4$, and the following rings are defined above.

The compound represented by the formula (cc) can be obtained by subjecting the compound represented by the formula (aa) and the compound represented by the formula (bb) to a reaction in the presence of a base such as potassium carbonate, a ligand such as triphenylphosphine, and a palladium catalyst such as tetrakis(triphenylphosphine)palladium. The compound represented by the formula (dd) can be obtained by subjecting the compound represented by the formula (cc) to catalytic hydrogenation in the presence of a catalyst such as palladium-active carbon in a solvent such as THF, methanol.

[Synthesis Method 2]

$R^4$ is tetrazolyl in the formula (I).

-continued

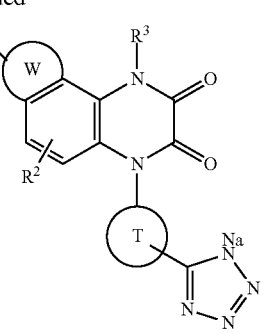

(f)

In the above-illustrated formula, $R^1$, $R^2$, $R^3$, and the following rings are defined above.

The tetrazole compound represented by the formula (e) can be obtained by reaction of the nitrile compound represented by the formula (p) with an azide compound such as tri-n-butyltin azide, sodium azide, in the presence of a solvent such as toluene, DMF.

The metal salt represented by the formula (f) can be obtained by reaction of the tetrazole compound represented by the formula (e) with an inorganic base such as sodium hydrogencarbonate, potassium hydrogencarbonate in the presence of a solvent such as water, ethanol.

[Synthesis Method 3]

(A) $R^4$ is benzenesulfonylamino optionally having one or more substituents in the formula (I).

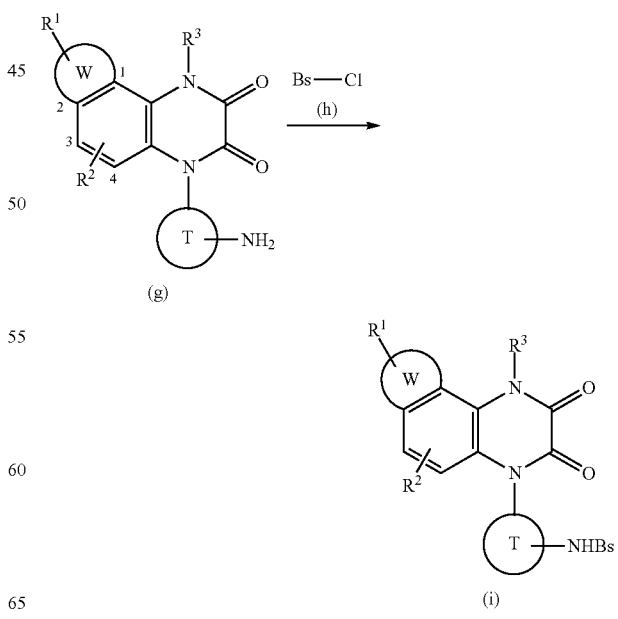

(B) $R^4$ is a $C_{1-8}$ alkylamino group in the formula (I).

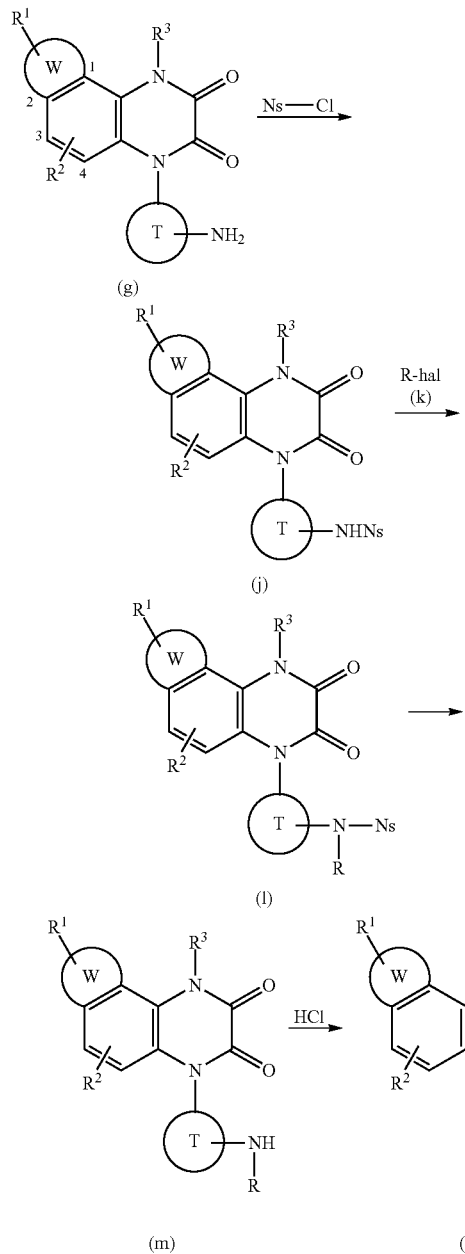

(g)

(j)

(l)

(m)    (n)

In the above-illustrated formulas (A) and (B), Bs is benzenesulfonyl optionally having one or more substituents, Ns is 2-nitrobenzenesulfonyl, R is a $C_{1-8}$ alkylamino group, and $R^1$, $R^2$, $R^4$, and the following rings are defined above.

(A)

The compound of the invention represented by the formula (I) can be obtained by reaction of the amino compound represented by the formula (g) with benzenesulfonyl chloride (BsCl) optionally having one or more substituents represented by the formula (h) in pyridine.

(B)

The compound represented by the formula (j) can be obtained by reaction of the amino compound represented by the formula (g) with 2-nitrobenzenesulfonyl chloride (NsCl) in pyridine. The compound represented by the formula (l) can be obtained by reaction of the compound (j) with the alkyl halide represented by the formula (k) in the presence of a base such as potassium carbonate in DMF. The compound represented by the formula (m) can be obtained by reaction of the compound (l) with thiophenol in the presence of a base such as potassium carbonate in DMF. The hydrochloride represented by the formula (n) can be obtained by reaction of the compound (m) with hydrogen chloride in a solvent such as methanol, chloroform.

The other compounds of the present invention represented by the formulas (I) and (II) can also be prepared by referring to the above-mentioned synthesis methods, the below described Examples, the patent documents described above, and the other known documents.

Examples of the obtained representative compounds of the present invention are shown below.

(Representative Compound 1)

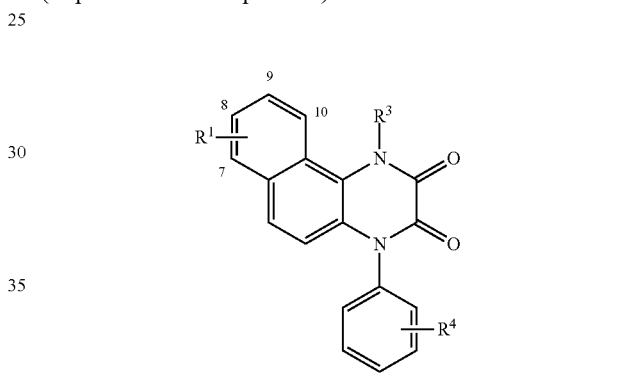

In the above-illustrated formula, $R^1$, $R^3$, and $R^4$ are shown in Tables 1 to 3.

TABLE 1

| $R^1$ | $R^3$ | $R^4$ |
|---|---|---|
| H | H | 3-OH |
| H | H | 3-OCH$_3$ |
| H | H | 4-OH |
| H | H | 4-OCH$_3$ |
| H | H | 2-OH |
| H | H | 2-OCH$_3$ |
| H | H | 2,3-OH |
| H | H | 3-OH, 4-F |
| H | H | 3,4-OH |
| H | H | 3,4-OCH$_3$ |
| H | H | 3,4,5-OCH$_3$ |
| H | H | 3-CN |

TABLE 2

| $R^1$ | $R^3$ | $R^4$ |
|---|---|---|
| H | H | 4-CN |
| H | H | 3-CO$_2$H |
| H | H | 3-CO$_2$CH$_3$ |
| H | H | 3-Br |
| H | H | 3-F |
| H | H | 4-CH$_3$ |

TABLE 2-continued

| R¹ | R³ | R⁴ |
|---|---|---|
| H | H | 3-NH₂ |
| H | H | 3-NHSO₂-phenyl |
| H | H | 3-NHSO₂-(2-NO₂) phenyl |
| H | H | 4-NHSO₂-phenyl |
| H | CH₃ | 3-NHSO₂-(2-NO₂) phenyl |
| H | C₂H₅ | 3-NHC₂H₅ |
| H | H | 3-CH₂OH |
| H | H | 4-CH₂OH |

TABLE 3

| R¹ | R³ | R⁴ |
|---|---|---|
| H | H | 3-CF₃ |
| H | H | 3-phenyl |
| H | H | 3-N(CH₃)₂ |
| H | H | 3,5-OH |
| H | H | 4-OCOCH₃ |
| H | H | 2-CH₃ |
| 9-CH₃ | H | 3-NH₂ |
| 9-Cl | H | 3-NH₂ |
| 8-CH₃ | H | 3-NH₂ |
| 8-Cl | H | 3-NH₂ |

(Representative Compound 2)

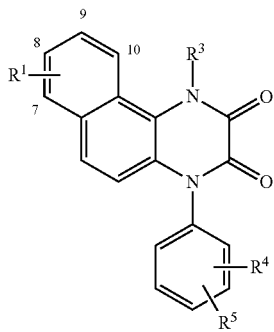

In the above-illustrated formula, R¹, R³, R⁴, and R⁵ are shown in Tables 4 to 6.

TABLE 4

| R¹ | R³ | * | R⁴ | R⁵ |
|---|---|---|---|---|
| H | H | 3 | 1H-tetrazol-5-yl | H |
| H | H | 4 | 1H-tetrazol-5-yl | H |
| 8-CH₃ | H | 3 | 1H-tetrazol-5-yl | H |
| 8-Cl | H | 3 | 1H-tetrazol-5-yl | H |
| H | H | 3 | 1H-tetrazol-5-yl | 4-F |
| H | H | 3 | 1H-tetrazol-5-yl | 4-CH₃ |
| H | H | 3 | 1H-tetrazol-5-yl | 5-Br |
| H | H | 3 | 1H-tetrazol-5-yl | 6-CH₃ |
| H | H | 3 | 1H-tetrazol-5-yl | 6-Cl |
| H | H | 3 | 5-thioxo-1,2,4-oxadiazol-3-yl | H |
| H | H | 3 | 5-oxo-1,2,4-oxadiazol-3-yl | H |
| H | H | 3 | 5-cyano-1H-1,2,3-triazol-4-yl | H |

(Remark)
*: The position of R⁴

TABLE 5

| R¹ | R³ | * | R⁴ | R⁵ |
|---|---|---|---|---|
| H | H | 3 | 1H-tetrazol-5-yl | 6-OH |
| H | H | 3 | 2-methyl-2H-tetrazol-5-yl | H |
| H | CH₃ | 3 | 2-methyl-2H-tetrazol-5-yl | H |
| H | C₂H₅ | 3 | 2-ethyl-2H-tetrazol-5-yl | H |
| H | H | 3 | 1-methyl-1H-tetrazol-5-yl | H |
| H | H | 3 | 4-methyl-5-thioxo-1,2,4-oxadiazol-3-yl | H |
| H | H | 3 | 1-methyl-1H-imidazol-2-yl | H |
| H | H | 3 | 1-methyl-1H-imidazol-4-yl | H |
| H | H | 3 | 1,3-oxazol-2-yl | H |
| H | H | 3 | 1,3-thiazol-2-yl | H |
| H | H | 3 | pyrrol-2-yl | H |
| H | H | 3 | thiophen-2-yl | H |
| H | H | 3 | 1H-imidazol-2-yl | H |
| H | H | 3 | 1H-imidazol-4-yl | H |

(Remark)
*: The position of R⁴

TABLE 6

| R¹ | R³ | * | R⁴ | R⁵ |
|---|---|---|---|---|
| H | H | 3 | pyrazol-5-yl | H |
| H | H | 3 | 5-chloro-1H-imidazol-2-yl | H |
| H | H | 3 | 5-trifluoromethyl-1H-imidazol-2-yl | H |
| H | H | 3 | 1,2,3-triazol-4-yl | H |
| H | H | 3 | 1,2,4-triazol-3-yl | H |
| H | H | 3 | 3-methyl-1,2,4-oxadiazol-5-yl | H |
| H | H | 3 | 3,5-dimethylisoxazol-4-yl | H |
| H | H | 3 | 1-tetrazol-1-yl | H |
| H | H | 3 | phenyl | H |
| H | H | 3 | pyridin-3-yl | H |
| H | H | 3 | pyrimidin-5-yl | H |
| H | H | 3 | 2-aminopyridin-5-yl | H |

(Remark)
*: The position of R⁴

(Representative Compound 3)

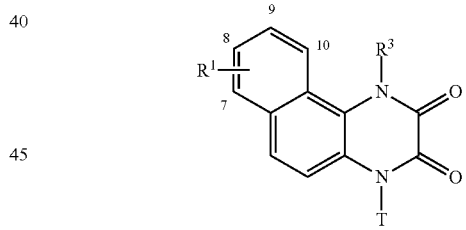

In the above-illustrated formula, R¹, R³, and T are shown in Tables 7 and 8.

TABLE 7

| R¹ | R³ | T |
|---|---|---|
| H | H | 1H-indol-6-yl |
| H | H | 1H-indolin-6-yl |
| H | H | 1H-indol-4-yl |
| H | H | 1H-indazol-6-yl |
| H | CH₃ | 1H-indazol-6-yl |
| H | C₂H₅ | 1H-indazol-6-yl |
| 8-CH₃ | H | 1H-indazol-6-yl |
| 8-Cl | H | 1H-indazol-6-yl |
| H | H | 1H-indazol-4-yl |
| H | H | 1H-benzimidazol-6-yl |
| H | H | 2-trifluoromethyl-1H-benzimidazol-6-yl |
| H | H | 1H-benzotriazol-6-yl |

TABLE 8

| R¹ | R³ | T |
|---|---|---|
| H | H | 3-methylbenzisoxazol-6-yl |
| H | H | pyridin-4-yl |
| H | H | 3-methoxypyridin-5-yl |
| H | H | 3-hydroxypyridin-5-yl |
| H | H | pyridine-3-yl |
| H | H | 7-hydroxyquinolin-3-yl |
| H | H | pyrrimidin-2-yl |
| H | H | thiophen-2-yl |
| H | H | pyridin-2-yl |
| H | H | 4-methylpyridin-2-yl |
| H | H | 2-bromopyridin-5-yl |

(Representative Compound 4)

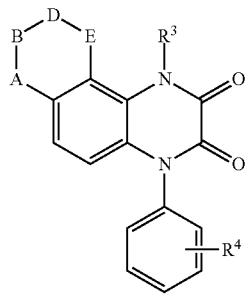

In the above-illustrated formula, A-B-D-E, $R^3$, and $R^4$ are shown in Tables 9 to 11.

TABLE 9

| A-B-D-E | R³ | R⁴ |
|---|---|---|
| CH₂—CH₂—CH₂—CH₂ | H | 3-OH |
| CH₂—CH₂—CH₂—CH₂ | H | 3-OCH₃ |
| CH₂—CH₂—CH₂—CH₂ | H | 4-OH |
| CH₂—CH₂—CH₂—CH₂ | H | 4-OCH₃ |
| CH₂—CH₂—CH₂—CH₂ | H | 2-OH |
| CH₂—CH₂—CH₂—CH₂ | H | 2-OCH₃ |
| CH₂—CH₂—CH₂—CH₂ | H | 2,3-OH |
| CH₂—CH₂—CH₂—CH₂ | H | 3-OH, 4-F |
| CH₂—CH₂—CH₂—CH₂ | H | 3,4-OH |
| CH₂—CH₂—CH₂—CH₂ | H | 3,4-OCH₃ |
| CH₂—CH₂—CH₂—CH₂ | H | 3,4,5-OCH₃ |
| CH₂—CH₂—CH₂—CH₂ | H | 3-CN |

TABLE 10

| A-B-D-E | R³ | R⁴ |
|---|---|---|
| CH₂—NH—CH₂—CH₂ | H | 4-CN |
| CH₂—CH₂—CH₂—CH₂ | H | 3-CO₂H |
| CH₂—NH—CH₂—CH₂ | H | 3-CO₂CH₃ |
| CH₂—CH₂—CH₂—CH₂ | H | 3-Br |
| CH₂—CH₂—NH—CH₂ | H | 3-F |
| CH₂—CH₂—O—CH₂ | H | 4-CH₃ |
| CH₂—CH₂—CH₂—CH₂ | H | 3-NH₂ |
| CH₂—CH₂—CH₂—CH₂ | H | 3-NHSO₂-phenyl |
| CH₂—CH₂—CH₂—CH₂ | H | 3-NHSO₂-(2-NO₂) phenyl |
| CH₂—CH₂—CH₂—CH₂ | H | 4-NHSO₂-phenyl |
| CH₂—CH₂—CH₂—CH₂ | CH₃ | 3-NHSO₂-(2-NO₂) phenyl |
| CH₂—CH₂—CH₂—CH₂ | C₂H₅ | 3-NHC₂H₅ |

TABLE 11

| A-B-D-E | R³ | R⁴ |
|---|---|---|
| CH₂—CH₂—CH₂—CH₂ | H | 3-CH₂OH |
| CH₂—CH₂—CH₂—CH₂ | H | 3-NHSO₂CH₃ |
| CH₂—CH₂—CH₂—CH₂ | H | 3-CF₃ |
| CH₂—CH₂—CH₂—CH₂ | H | 3-phenyl |
| CH₂—CH₂—CH₂—CH₂ | H | 3-N(CH₃)₂ |
| CH₂—CH₂—CH₂—CH₂ | H | 3,5-OH |
| CH₂—CH₂—CH₂—CH₂ | H | 4-OCOCH₃ |
| CH₂—CH₂—CH₂—CH₂ | H | 2-CH₃ |
| CH₂—CH(CH₃)—CH₂—CH₂ | H | 3-NH₂ |

(Representative Compound 5)

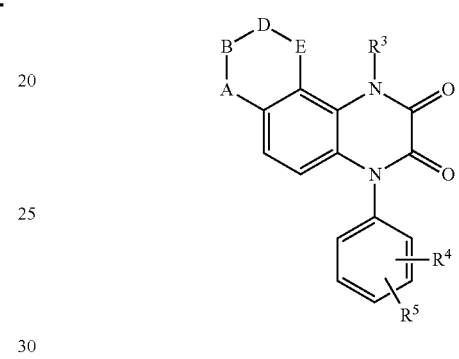

In the above-illustrated formula, A-B-D-E, $R^3$, $R^4$, and $R^5$ are shown in Tables 12 to 14.

TABLE 12

| A—B—D—E | R³ | * | R⁴ | R⁵ |
|---|---|---|---|---|
| CH₂—CH₂—CH₂—CH₂ | H | 3 | 1H-tetrazol-5-yl | H |
| CH₂—CH₂—CH₂—CH₂ | H | 4 | 1H-tetrazol-5-yl | H |
| CH₂—NH—CH₂—CH₂ | H | 3 | 1H-tetrazol-5-yl | H |
| CH₂—CH₂—O—CH₂ | H | 3 | 1H-tetrazol-5-yl | 4-F |
| CH₂—CH₂—CH₂—CH₂ | H | 3 | 1H-tetrazol-5-yl | 4-CH₃ |
| CH₂—CH₂—CH₂—CH₂ | H | 3 | 1H-tetrazol-5-yl | 5-Br |
| CH₂—CH₂—CH₂—CH₂ | H | 3 | 1H-tetrazol-5-yl | 6-CH₃ |
| CH₂—CH₂—CH₂—CH₂ | H | 3 | 1H-tetrazol-5-yl | 6-Cl |
| CH₂—CH₂—CH₂—CH₂ | H | 3 | 5-thioxo-1,2,4-oxadiazol-3-yl | H |
| CH₂—CH₂—CH₂—CH₂ | H | 4 | 5-oxo-1,2,4-oxadiazol-3-yl | H |

(Remark)
*: The position of $R^4$

TABLE 13

| A—B—D—E | R³ | * | R⁴ | R⁵ |
|---|---|---|---|---|
| CH₂—CH₂—CH₂—CH₂ | H | 3 | 5-cyano-1H-1,2,3-triazol-4-yl | H |
| CH₂—CH₂—CH₂—CH₂ | H | 3 | 1H-tetrazol-5-yl | 6-OH |
| CH₂—CH₂—CH₂—CH₂ | H | 3 | 2-methyl-2H-tetrazol-5-yl | H |
| CH₂—CH₂—CH₂—CH₂ | CH₃ | 3 | 2-methyl-2H-tetrazol-5-yl | H |
| CH₂—CH₂—CH₂—CH₂ | C₂H₅ | 3 | 2-ethyl-2H-tetrazol-5-yl | H |
| CH₂—NH—CH₂—CH₂ | H | 3 | 1-methyl-1H-tetrazol-5-yl | H |
| CH₂—CH₂—CH₂—CH₂ | H | 3 | 4-methyl-5-thioxo-1,2,4-oxadiazol-3-yl | H |
| CH₂—CH₂—CH₂—CH₂ | H | 3 | 1-methyl-1H-imidazol-2-yl | H |
| CH₂—CH₂—CH₂—CH₂ | H | 3 | 1-methyl-1H-imidazol-4-yl | H |
| CH₂—CH₂—CH₂—CH₂ | H | 3 | 1,3-oxazol-2-yl | H |
| CH₂—CH₂—CH₂—CH₂ | H | 3 | 1,3-thiazol-2-yl | H |
| CH₂—CH₂—CH₂—CH₂ | H | 3 | pyrrol-2-yl | H |
| CH₂—CH₂—CH₂—CH₂ | H | 3 | thiophen-2-yl | H |

(Remark)
*: The position of $R^4$

TABLE 14

| A—B—D—E | R³ | * | R⁴ | R⁵ |
|---|---|---|---|---|
| CH₂—CH₂—CH₂—CH₂ | H | 3 | 1H-imidazol-2-yl | H |
| CH₂—CH₂—CH₂—CH₂ | H | 3 | 1H-imidazol-4-yl | H |
| CH₂—CH₂—CH₂—CH₂ | H | 4 | pyrazol-4-yl | H |
| CH₂—CH₂—CH₂—CH₂ | H | 3 | 5-chloro-1H-imidazol-2-yl | H |
| CH₂—CH₂—CH₂—CH₂ | H | 3 | 5-trifluoromethyl-1H-imidazol-2-yl | H |
| CH₂—CH₂—CH₂—CH₂ | H | 3 | 1,2,3-triazol-4-yl | H |
| CH₂—CH₂—CH₂—CH₂ | H | 3 | 1,2,4-triazol-3-yl | H |
| CH₂—CH₂—CH₂—CH₂ | H | 3 | 3-methyl-1,2,4-oxadiazol-5-yl | H |
| CH₂—CH₂—CH₂—CH₂ | H | 3 | 3,5-dimethylisoxazol-4-yl | H |
| CH₂—CH₂—CH₂—CH₂ | H | 3 | 1-tetrazol-1-yl | H |
| CH₂—CH(CH₃)—CH₂—CH₂ | H | 3 | phenyl | H |
| CH₂—CH₂—CH(CH₃)—CH₂ | H | 3 | pyrimidin-5-yl | H |

(Remark)
*: The position of R⁴

(Representative Compound 6)

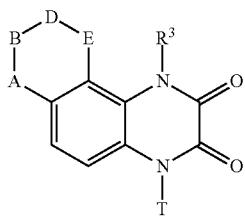

In the above-illustrated formula, A-B-D-E, R³, and T are shown in Tables 15 and 16.

TABLE 15

| A—B—D—E | R³ | T |
|---|---|---|
| CH₂—CH₂—CH₂—CH₂ | H | 1H-indol-6-yl |
| CH₂—CH₂—CH₂—CH₂ | H | 1H-indolin-6-yl |
| CH₂—CH₂—CH₂—CH₂ | H | 1H-indol-4-yl |
| CH₂—CH₂—CH₂—CH₂ | H | 1H-indazol-6-yl |
| CH₂—CH₂—CH₂—CH₂ | CH₃ | 1H-indazol-6-yl |
| CH₂—CH₂—CH₂—CH₂ | C₂H₅ | 1H-indazol-6-yl |
| CH₂—CH₂—CH₂—CH₂ | H | 1H-indazol-4-yl |
| CH₂—CH₂—CH₂—CH₂ | H | 1H-benzimidazol-6-yl |
| CH₂—CH₂—CH₂—CH₂ | H | 2-trifluoromethyl-1H-benzimidazol-6-yl |
| CH₂—CH₂—CH₂—CH₂ | H | 1H-benzotriazol-6-yl |
| CH₂—CH₂—CH₂—CH₂ | H | 3-methylbenzisoxazol-6-yl |

TABLE 16

| A—B—D—E | R³ | T |
|---|---|---|
| CH₂—CH₂—CH₂—CH₂ | H | pyridin-4-yl |
| CH₂—CH₂—CH₂—CH₂ | H | 3-methoxypyridin-5-yl |
| CH₂—CH₂—CH₂—CH₂ | H | 3-hydroxypyridin-5-yl |
| CH₂—CH₂—CH₂—CH₂ | H | pyridine-3-yl |
| CH₂—CH₂—CH₂—CH₂ | H | 7-hydroxyquinolin-3-yl |
| CH₂—CH₂—CH₂—CH₂ | H | pyrrimidin-2-yl |
| CH₂—CH₂—CH₂—CH₂ | H | thiophen-2-yl |
| CH₂—CH₂—CH₂—CH₂ | H | pyridin-2-yl |
| CH₂—CH₂—CH₂—CH₂ | H | 4-methylpyridin-2-yl |
| CH₂—CH₂—CH₂—CH₂ | H | 2-bromopyridin-5-yl |
| CH₂—CH(CH₃)—CH₂—CH₂ | H | 1H-indol-6-yl |
| CH₂—CH(CH₃)—CH₂—CH₂ | H | 1H-indol-5-yl |
| CH₂—CH(CH₃)—CH₂—CH₂ | H | 1H-indol-4-yl |

(Representative Compound 7)

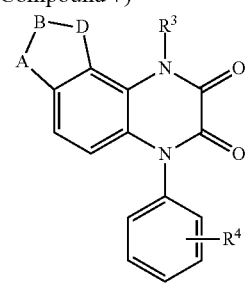

In the above-illustrated formula, A-B-D, R³, and R⁴ are shown in Tables 17 to 19.

TABLE 17

| A—B—D | R³ | R⁴ |
|---|---|---|
| CH₂—CH₂—CH₂ | H | 3-OH |
| CH₂—CH₂—CH₂ | H | 3-OCH₃ |
| CH₂—CH₂—CH₂ | H | 4-OH |
| CH₂—CH₂—CH₂ | H | 4-OCH₃ |
| O—CH₂—O | H | 2,3-OH |
| CH₂—CH₂—CH₂ | H | 3,4-OH |
| NH—CH₂—CH₂ | H | 3,4,5-OCH₃ |
| CH₂—CH₂—CH₂ | H | 3-CN |

TABLE 18

| A—B—D | R³ | R⁴ |
|---|---|---|
| CH₂—CH₂—CH₂ | H | 3-CO₂H |
| O—CH₂—O | H | 3-Br |
| CH₂—CH₂—CH₂ | H | 4-CH₃ |
| CH₂—NH—CH₂ | H | 4-NHSO₂-phenyl |
| CH₂—CH₂—CH₂ | H | 3-NHSO₂-(2-NO₂)phenyl |
| CH₂—CH₂—CH₂ | H | 4-NHSO₂-phenyl |
| CH₂—CH₂—CH₂ | CH₃ | 3-NHSO₂-(2-NO₂)phenyl |
| CH₂—CH₂—CH₂ | C₂H₅ | 3-NHC₂H₅ |

TABLE 19

| A—B—D | R³ | R⁴ |
|---|---|---|
| CH₂—CH₂—CH₂ | H | 3-NHSO₂CH₃ |
| CH₂—CH₂—CH₂ | H | 3-phenyl |
| CH₂—CH₂—CH₂ | H | 3-N(CH₃)₂ |
| CH₂—CH₂—NH | H | 2-CH₃ |
| CH₂—CH(CH₃)—CH₂ | H | 3-NH₂ |
| CH₂—CH(CH₃)—CH₂ | H | 4-NH₂ |

(Representative Compound 8)

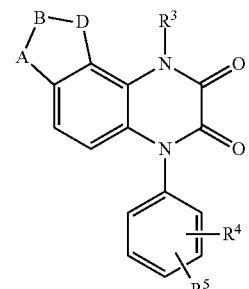

In the above-illustrated formula, A-B-D, R³, R⁴, and R⁵ are shown in Tables 20 to 22.

TABLE 20

| A—B—D | R³ | * | R⁴ | R⁵ |
|---|---|---|---|---|
| CH₂—CH₂—CH₂ | H | 3 | 1H-tetrazol-5-yl | H |
| O—CH₂—O | H | 4 | 1H-tetrazol-5-yl | H |
| CH₂—CH(CH₃)—CH₂ | H | 3 | 1H-tetrazol-5-yl | H |
| CH₂—CH(CH₃)—CH₂ | H | 4 | 1H-tetrazol-5-yl | H |
| CH₂—CH₂—CH₂ | H | 3 | 1H-tetrazol-5-yl | 4-F |
| CH₂—CH₂—CH₂ | H | 3 | 1H-tetrazol-5-yl | 4-CH₃ |
| CH₂—CH₂—CH₂ | H | 3 | 1H-tetrazol-5-yl | 5-Br |
| CH₂—NH—CH₂ | H | 3 | 1H-tetrazol-5-yl | 6-CH₃ |
| CH₂—CH₂—CH₂ | H | 3 | 5-thioxo-1,2,4-oxadiazol-3-yl | H |

(Remark)
*: The position of R⁴

TABLE 21

| A—B—D | R³ | * | R⁴ | R⁵ |
|---|---|---|---|---|
| CH₂—CH₂—CH₂ | H | 3 | 1H-tetrazol-5-yl | 6-OH |
| CH₂—CH₂—CH₂ | H | 3 | 2-methyl-2H-tetrazol-5-yl | H |
| CH₂—CH₂—CH₂ | CH₃ | 3 | 2-methyl-2H-tetrazol-5-yl | H |
| CH₂—CH₂—CH₂ | C₂H₅ | 3 | 2-ethyl-2H-tetrazol-5-yl | H |
| CH₂—CH₂—CH₂ | H | 3 | 4-methyl-5-thioxo-1,2,4-oxadiazol-3-yl | H |
| CH₂—CH₂—CH₂ | H | 3 | 1-methyl-1H-imidazol-2-yl | H |
| CH₂—CH₂—CH₂ | H | 3 | 1,3-oxazol-2-yl | H |
| CH₂—CH₂—CH₂ | H | 3 | 1,3-thiazol-2-yl | H |
| CH₂—CH₂—CH₂ | H | 3 | thiophen-2-yl | H |

(Remark)
*: The position of R⁴

TABLE 22

| A—B—D | R³ | * | R⁴ | R⁵ |
|---|---|---|---|---|
| CH₂—CH₂—CH₂ | H | 3 | 1H-imidazol-4-yl | H |
| CH₂—CH₂—CH₂ | H | 3 | pyrazol-4-yl | H |
| CH₂—CH₂—CH₂ | H | 3 | 5-chloro-1H-imidazol-2-yl | H |
| CH₂—CH₂—CH₂ | H | 3 | 1,2,4-triazol-3-yl | H |
| CH₂—CH₂—CH₂ | H | 3 | 1-tetrazol-1-yl | H |
| O—CH₂—O | H | 3 | phenyl | H |
| CH₂—CH₂—CH₂ | H | 3 | pyridin-3-yl | H |
| NH—CH₂—CH₂ | H | 3 | pyrimidin-5-yl | H |

(Remark)
*: The position of R⁴

(Representative Compound 9)

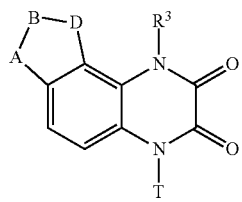

In the above-illustrated formula, A-B-D, R³, and T are shown in Tables 23 and 24.

TABLE 23

| A—B—D | R³ | T |
|---|---|---|
| CH₂—CH₂—CH₂ | H | 1H-indol-6-yl |
| O—CH₂—O | H | 1H-indolin-6-yl |
| CH₂—CH₂—CH₂ | CH₃ | 1H-indazol-6-yl |
| CH₂—CH₂—CH₂ | C₂H₅ | 1H-indazol-6-yl |
| CH₂—CH₂—CH₂ | H | 1H-indazol-4-yl |

TABLE 23-continued

| A—B—D | R³ | T |
|---|---|---|
| CH₂—NH—CH₂ | H | 1H-benzotriazol-6-yl |
| CH₂—CH₂—CH₂ | H | 3-methylbenzisoxazol-6-yl |

TABLE 24

| A—B—D | R³ | T |
|---|---|---|
| CH₂—CH₂—CH₂ | H | pyridin-4-yl |
| CH₂—CH₂—CH₂ | H | thiophen-2-yl |
| CH₂—NH—CH₂ | H | 4-methylpyridin-2-yl |
| CH₂—CH(CH₃)—CH₂ | H | 1H-indol-6-yl |

The pharmacological effects of the present invention are described below.

$P2X_4$ antagonism of the compound of the present invention is measured as described below.

1321N1 cells stably expressing human $P2X_4$ receptors were plated in 96-well assay plate and cultured 24 hours at 37° C. in an atmosphere of 5% $CO_2$ for intracellular calcium assay. Fura-2 AM calcium fluorescent indicator was used for the intracellular calcium assay. Fura-2 AM was dissolved in an assay buffer, and the solution was loaded onto cells. The obtained plate was used for fluorescent assay. Test compounds were treated to cells 15 minutes before the addition of ATP, and the response to intracellular calcium influx induced by addition of ATP was monitored by a micro plate reader. The fluorescence ratio of excitations wavelengths of 340 nm and 380 nm was used as the index of intracellular calcium change. The inhibition activities of the test compounds were calculated by comparison with the absence of the test compound (control).

As is evident from the below-described results shown in Examples 30 and 31, the compound of the present invention shows excellent $P2X_4$ receptor antagonism (Tables 25 and 26).

Therefore, it is considered that the diazepine derivative represented by the formula (I), (II), or its pharmacologically acceptable salt, which shows $P2X_4$ receptor antagonism, is effective as an agent for prevention or treatment of nociceptive, inflammatory, and neuropathic pains. In more detail, it is effective as a preventive or therapeutic agent for pains caused by various cancers, diabetic neuritis, viral diseases such as herpes, and osteoarthritis. The preventive or therapeutic agent of the present invention can also be used in combination with other agents such as opioid analgesic (e.g., morphine, fentanyl), sodium channel inhibitor (e.g., novocaine, lidocaine), or NSAIDs (e.g., aspirin, ibuprofen). The agent for pains caused by cancers can be used in combination with a carcinostatic such as a chemotherapic.

The compound of the present invention can be administered to human beings by ordinary administration methods such as oral administration or parenteral administration.

The compound can be granulated in ordinary manners for the preparation of pharmaceuticals. For instance, the compound can be processed to give pellets, granule, powder, capsule, suspension, injection, suppository, and the like.

Ordinary additives such as vehicles, disintegrators, binders, lubricants, dyes, and diluents are used for the preparation of these pharmaceuticals. As the vehicles, lactose, D-mannitol, crystalline cellulose, and glucose can be mentioned. Further, there can be mentioned starch and carboxymethylcellulose calcium (CMC-Ca) as the disintegrators, magnesium stearate and talc as the lubricants, and hydroxypropylcellulose (HPC), gelatin and polyvinylpirrolidone (PVP) as the binders. The preparation of an injection can be made using solvents, stabilizers, dissolution-aids, suspensions, emulsifiers, soothing agents, buffers, or preservatives.

The compound of the invention can be administered to an adult generally in an amount of approx. 0.01 mg to 100 mg a day by parenteral administration and 1 mg to 2,000 mg a day by oral administration. The dosage can be adjusted in consideration of age and conditions of the patient.

The present invention is further described by the following non-limiting examples.

EXAMPLES

Example 1

4-(3-Cyanophenyl)-1,4-dihydrobenzo[f]quinoxaline-2,3-dione (1) 3-(1-Nitro-2-naphthylamino)benzonitrile An anhydrous toluene (40 mL) suspension of 1-nitronaphthalen-2-yl triflate (3.00 g, 8.64 mmol), 3-aminobenzonitrile (1.02 g, 8.64 mmol), potassium carbonate (1.19 g, 8.64 mmol), triphenylphosphine (227 mg, 0.864 mmol), and tetrakis(triphenylphosphine)palladium (500 mg, 0.432 mmol) was stirred at 110° C. for 18 hours. After cooling on standing, the reaction mixture was filtered, and the filtrate was diluted with ethyl acetate. The obtained organic solution was washed with a saturated aqueous sodium hydrogen carbonate solution, and dried over anhydrous sodium sulfate. The solvent was removed by evaporation under reduced pressure, and the residue was purified by silica gel column chromatography (chloroform/methanol=99/1) to obtain the titled compound as a yellow powder (1.60 g, yield 64%).

$^1$H NMR (CDCl$_3$, 400 MHz) δ: 7.37 (1H, d, J=9 Hz), 7.4-7.6 (5H, m), 7.66 (1H, t, J=8 Hz), 7.78 (1H, d, J=8 Hz), 7.86 (1H, d, J=9 Hz), 8.38 (1H, d, J=8 Hz), 8.97 (1H, br s).

(2) 3-(1-Amino-2-naphthylamino)benzonitrile

To a methanol (10 mL) and an anhydrous tetrahydrofuran (50 mL) solution of 3-(1-nitro-2-naphthylamino)benzonitrile (1.60 g, 5.53 mmol) was added 10% palladium-active carbon (160 mg), and the mixture was hydrogenated for 4 hours at room temperature under atmospheric pressure. After removal of the catalyst by filtration, the solvent was removed by evaporation under reduced pressure. The residue was purified by silica gel column chromatography (hexane/ethyl acetate=7/3) to obtain the titled compound as a pale brown powder (1.06 g, yield 74%).

$^1$H NMR (DMSO-d$_6$, 400 MHz) δ: 5.40 (2H, s), 6.83 (1H, t, J=2 Hz), 6.91 (1H, dd, J=2 Hz, 8 Hz), 7.02 (1H, d, J=7 Hz), 7.16 (1H, d, J=10 Hz), 7.18 (1H, d, J=10 Hz), 7.28 (1H, t, J=8 Hz), 7.3-7.5 (2H, m), 7.7-7.8 (1H, m), 7.83 (1H, s), 8.1-8.2 (1H, m).

(3) 4-(3-Cyanophenyl)-1,4-dihydrobenzo[f]quinoxaline-2,3-dione

To an anhydrous tetrahydrofuran (18 mL) solution of 3-(1-amino-2-naphthylamino)benzonitrile (200 mg, 0.771 mmol) was added an anhydrous tetrahydrofuran (2 mL) solution of oxalyl chloride (66 μL, 0.771 mmol) under cooling in an ice-bath. The mixture was stirred under cooling in an ice-bath for 30 minutes and at room temperature for one hour. After addition of methanol (1 mL), the solvent was removed by evaporation under reduced pressure. The mixture was suspended by chloroform, and washed with a saturated aqueous sodium hydrogen carbonate solution. The precipitated solid was collected by filtration, and washed with water. The obtained solid was purified by silica gel chromatography (chloroform/methanol=9/1) to obtain the titled compound as a white powder (23 mg, yield 10%).

$^1$H NMR (DMSO-d$_6$, 400 MHz) δ: 6.59 (1H, d, J=9 Hz), 7.5-7.7 (3H, m), 7.8-8.0 (3H, m), 8.03 (1H, s), 8.08 (1H, d, J=8 Hz), 8.68 (1H, d, J=8 Hz), 12.37 (1H, br s).

FAB-MS (m/z): 314 (M+1).

Example 2

4-[3-(1H-Tetrazol-5-yl)phenyl]-1,4-dihydrobenzo[f]quinoxaline-2,3-dione sodium salt (1) 4-[3-(1H-Tetrazol-5-yl)phenyl]-1,4-dihydrobenzo[f]quinoxaline-2,3-dione To an anhydrous toluene (1 mL)-anhydrous DMF (1.5 mL) solution of 4-(3-cyanophenyl)-1,4-dihydrobenzo[f]quinoxaline-2,3-dione (20 mg, 0.064 mmol) was added tri-n-butyltin azide (53 μL, 0.192 mmol), and the mixture was stirred at 110° C. for 18 hours. After cooling on standing, the reaction mixture was poured into a 1M aqueous sodium hydroxide solution, and washed with ethyl acetate. After neutralization of the aqueous layer by addition of a 1M aqueous hydrochloric acid solution, the precipitated solid was collected by filtration, washed with water, and dried to obtain the titled compound as a white crystal (15 mg, yield 66%).

$^1$H NMR (DMSO-d$_6$, 400 MHz) δ: 6.67 (1H, d, J=9 Hz), 7.5-7.7 (4H, m), 7.8-8.0 (2H, m), 8.13 (1H, s), 8.23 (1H, d, J=7 Hz), 8.69 (1H, d, J=8 Hz), 12.34 (1H, br s).

(2) 4-[3-(1H-Tetrazol-5-yl)phenyl]-1,4-dihydrobenzo[f]quinoxaline-2,3-dione sodium salt To an ethanol (1 mL)/water (0.5 mL) suspension of 4-[3-(1H-tetrazol-5-yl)phenyl]-1,4-dihydrobenzo[f]quinoxaline-2,3-dione (15 mg, 0.042 mmol) was added sodium hydrogen carbonate (3.5 mg, 0.042 mmol). After heating the mixture to form a solution, the solution was stirred at room temperature for 30 minutes, and concentrated under reduced pressure to obtain the titled compound as a pale yellow powder (7.3 mg, yield 46%).

$^1$H NMR (DMSO-d$_6$, 400 MHz) δ: 6.68 (1H, d, J=8 Hz), 7.28 (1H, d, J=7 Hz), 7.4-7.5 (2H, m), 7.58 (1H, t, J=8 Hz), 7.65 (1H, t, J=8 Hz), 7.84 (1H, d, J=8 Hz), 7.94 (1H, s), 8.17 (1H, d, J=8 Hz), 8.73 (1H, d, J=8 Hz), 12.28 (1H, br s).

FAB-MS (m/z): 379 (M+1).

Example 3

4-(3-Methoxyphenyl)-1,4-dihydrobenzo[f]quinoxaline-2,3-dione

To an anhydrous tetrahydrofuran (10 mL) solution of oxalyl chloride (162 μL, 1.89 mmol) was dropwise added an anhydrous tetrahydrofuran (10 mL) solution of N$^2$-(3-methoxyphenyl)naphthalene-1,2-diamine (500 mg, 1.89 mmol) under cooling in an ice-bath. The mixture was stirred under cooling in an ice-bath for 30 minutes and at room temperature for one hour. The reaction mixture was poured into a saturated aqueous sodium hydrogen carbonate solution, and extracted with ethyl acetate. The organic layer was dried over anhydrous sodium sulfate, and purified by silica gel chromatography (chloroform/methanol=97/3) after removing the solvent by evaporation under reduced pressure. The obtained solid was washed with ethyl acetate/methanol (=1/1) to obtain the titled compound as a slightly beige crystal (572 mg, yield 95%).

$^1$H NMR (DMSO-$d_6$, 400 MHz) δ: 3.79 (3H, s), 6.62 (1H, d, J=9 Hz), 7.00 (1H, d, J=8 Hz), 7.06 (1H, t, J=2 Hz), 7.15 (1H, dd, J=2 Hz, 8 Hz), 7.4-7.7 (4H, m), 7.89 (1H, d, J=8 Hz), 8.66 (1H, d, J=8 Hz), 12.32 (1H, br s).

FAB-MS (m/z): 319 (M+1).

Example 4

4-(3-Hydroxyphenyl)-1,4-dihydrobenzo[f]quinoxaline-2,3-dione sodium salt (1) 4-(3-Hydroxyphenyl)-1,4-dihydrobenzo[f]quinoxaline-2,3-dione To an anhydrous dichloromethane (5 mL) suspension of 4-(3-methoxyphenyl)-1,4-dihydrobenzo[f]quinoxaline-2,3-dione (562 mg, 1.77 mmol) was added 1M boron tribromide/dichloromethane solution (2.12 mL, 2.12 mmol) under cooling in an ice-bath, and the mixture was stirred at room temperature for 18 hours. The reaction mixture was poured into saturated aqueous sodium hydrogen carbonate solution. The precipitated solid was washed with water and ethanol. The solid was further washed with hexane, and dried to obtain the titled compound as an off-white crystal (280 mg, yield 52%).

$^1$H NMR (DMSO-$d_6$, 400 MHz) δ: 6.65 (1H, d, J=9 Hz), 6.7-6.9 (2H, m), 6.96 (1H, d, J=8 Hz), 7.43 (1H, t, J=8 Hz), 7.51 (1H, t, J=7 Hz), 7.5-7.7 (2H, m), 7.89 (1H, d, J=8 Hz), 8.66 (1H, d, J=8 Hz), 9.89 (1H, s), 12.28 (1H, br s).

(2) 4-(3-Hydroxyphenyl)-1,4-dihydrobenzo[f]quinoxaline-2,3-dione sodium salt

To a tetrahydrofuran (2 mL) suspension of 4-(3-hydroxyphenyl)-1,4-dihydrobenzo[f]quinoxaline-2,3-dione (27 mg, 0.089 mmol) was added a 1M sodium hydroxide aqueous solution (89 μL, 0.089 mmol), and the mixture was stirred at room temperature for one hour. After filtering the reaction mixture, the solvent was removed by evaporation under reduced pressure to obtain the titled compound as a slightly brown powder (24 mg, yield 83%).

$^1$H NMR (DMSO-$d_6$, 400 MHz) δ: 6.55 (1H, d, J=9 Hz), 6.6-6.7 (2H, m), 6.90 (1H, d, J=9 Hz), 7.19 (1H, d, J=9 Hz), 7.3-7.5 (3H, m), 7.69 (1H, d, J=8 Hz), 8.73 (1H, d, J=8 Hz).

FAB-MS (m/z): 327 (M+1).

Example 5

5-(3-Methoxyphenyl)-1,4,7,8,9,10-hexahydrobenzo[f]quinoxaline-2,3-dione (1) 1-Nitro-5,6,7,8-tetrahydronaphthalen-2-yl triflate To a dichloromethane (140 mL) solution of 1-nitro-5,6,7,8-tetrahydro-2-naphthol (8.78 g, 45.4 mmol) was added triethylamine (6.96 mL, 50.0 mmol). To the mixture was added dropwise trifluoromethanesulfonic anhydride (7.45 mL, 45.4 mmol) at 3° C. less than under cooling in an ice-bath. The mixture was stirred at room temperature for 18 hours. To the reaction mixture was added ice-cold water, and the mixture was extracted with dichloromethane. The organic layer was washed with water, and dried over anhydrous sodium sulfate. After removing the solvent by evaporation under reduced pressure, the residue was purified by silica gel column chromatography (hexane/ethyl acetate=8/1) to obtain the titled compound as a yellow oil (13.1 g, yield 89%).

$^1$H NMR (CDCl$_3$, 400 MHz) δ: 1.7-1.9 (4H, m), 2.6-2.9 (4H, m), 7.1-7.4 (2H, m).

(2) 1-Nitro-2-(3-methoxyphenyl)amino-5,6,7,8-tetrahydronaphthalene

1-Nitro-5,6,7,8-tetrahydronaphthalen-2-yl triflate and m-anisidine were used in a process similar to Example 1(1) to give the titled compound.

$^1$H NMR (CDCl$_3$, 400 MHz) δ: 1.7-1.9 (4H, m), 2.6-2.9 (4H, m), 3.78 (3H, s), 6.57 (1H, dd, J=2 Hz, 8 Hz), 6.62 (1H, s), 6.66 (1H, d, J=8 Hz), 7.0-7.3 (4H, m).

(3) 1-Amino-2-(3-methoxyphenyl)amino-5,6,7,8-tetrahydronaphthalene

1-Nitro-2-(3-methoxyphenyl)amino-5,6,7,8-tetrahydronaphthalene was used in a process similar to Example 1(2) to give the titled compound.

$^1$H NMR (CDCl$_3$, 400 MHz) δ: 1.7-1.8 (2H, m), 1.8-2.0 (2H, m), 2.4-2.6 (2H, m), 2.7-2.8 (2H, m), 3.74 (3H, s), 3.79 (1H, br s), 5.07 (1H, br s), 6.23 (1H, s), 6.29 (1H, d, J=8 Hz), 6.34 (1H, d, J=8 Hz), 6.52 (1H, d, J=8 Hz), 6.90 (1H, d, J=8 Hz), 7.08 (1H, d, J=8 Hz).

(4) 5-(3-Methoxyphenyl)-1,4,7,8,9,10-hexahydrobenzo[f]quinoxaline-2,3-dione

1-Amino-2-(3-methoxyphenyl)amino-5,6,7,8-tetrahydronaphthalene and oxalyl chloride were used in a process similar to Example 1(3) to give the titled compound.

$^1$H NMR (CDCl$_3$, 400 MHz) δ: 1.7-1.9 (2H, m), 1.9-2.0 (2H, m), 2.6-2.8 (4H, m), 3.83 (3H, s), 6.36 (1H, d, J=9 Hz), 6.7-6.8 (2H, m), 6.86 (1H, d, J=8 Hz), 7.07 (1H, dd, J=2 Hz, 8 Hz), 7.49 (1H, t, J=8 Hz), 8.78 (1H, br s).

IR (cm$^{-1}$, KBr): 3068, 2937, 1699, 1604, 1493, 1377, 1255, 1036, 804, 791, 706.

FAB-MS (m/z): 323 (M+1).

Example 6

5-(3-Hydroxyphenyl)-1,4,7,8,9,10-hexahydrobenzo[f]quinoxaline-2,3-dione 5-(3-Methoxyphenyl)-1,4,7,8,9,10-hexahydrobenzo[f]quinoxaline-2,3-dione was used in a process similar to Example 4(1) to give the titled compound.

$^1$H NMR (CDCl$_3$, 400 MHz) δ: 1.7-1.9 (2H, m), 1.9-2.0 (2H, m), 2.7-2.8 (4H, m), 6.41 (1H, d, J=8 Hz), 6.6-6.8 (2H, m), 6.78 (1H, d, J=9 Hz), 7.00 (1H, d, J=9 Hz), 7.40 (1H, t, J=8 Hz).

IR (cm$^{-1}$, KBr): 2941, 1689, 1599, 1489, 1377, 1269, 1232, 1188, 1147, 806, 706.

FAB-MS (m/z): 309 (M+1).

Example 7

4-(3-Aminophenyl)-1,4,7,8,9,10-hexahydrobenzo[f]quinoxaline-2,3-dione hydrochloride (1) 1-Nitro-2-(3-tert-butoxycarbonylaminophenyl)amino-5,6,7,8-tetrahydronaphthalene 1-Nitro-5,6,7,8-tetrahydronaphthalen-2-yl triflate and tert-butyl 3-aminophenylcarbamate were used in a process similar to Example 1(1) to give the titled compound.

¹H NMR (CDCl₃, 400 MHz) δ: 1.51 (9H, s), 1.7-1.8 (4H, m), 2.7-2.8 (4H, m), 6.44 (1H, br s), 6.75 (1H, dd, J=2 Hz, 8 Hz), 6.89 (1H, dd, J=2 Hz, 8 Hz), 7.0-7.1 (2H, m), 7.1-7.2 (2H, m), 7.26 (1H, br s).

(2) 1-Amino-2-(3-tert-butoxycarbonylaminophenyl) amino-5,6,7,8-tetrahydronaphthalene 1-Nitro-2-(3-tert-butoxycarbonylaminophenyl)amino-5,6,7,8-tetrahydronaphthalene was used in a process similar to Example 1(2) to give the titled compound.
¹H NMR (CDCl₃, 400 MHz) δ: 1.49 (9H, s), 1.7-2.0 (4H, m), 2.4-2.6 (2H, m), 2.7-2.8 (2H, m), 3.80 (2H, br s), 5.08 (1H, br s), 6.2-6.4 (2H, m), 6.52 (1H, d, J=8 Hz), 6.7-6.8 (2H, m), 6.89 (1H, d, J=8 Hz), 7.06 (1H, t, J=8 Hz).

(3) 4-(3-tert-Butoxycarbonylaminophenyl)-1,4,7,8,9,10-hexahydrobenzo[f]quinoxaline-2,3-dione 1-Amino-2-(3-tert-butoxycarbonylaminophenyl)amino-5,6,7,8-tetrahydronaphthalene and oxalyl chloride were used in a process similar to Example 1(3) to give the titled compound.
¹H NMR (CDCl₃, 400 MHz) δ: 1.49 (9H, s), 1.7-1.9 (2H, m), 1.9-2.0 (2H, m), 2.6-2.8 (4H, m), 6.37 (1H, d, J=8 Hz), 6.6-6.7 (1H, m), 6.77 (1H, d, J=9 Hz), 6.92 (1H, dt, J=2 Hz, 8 Hz), 7.4-7.5 (3H, m), 8.81 (1H, br s).

(4) 4-(3-Aminophenyl)-1,4,7,8,9,10-hexahydrobenzo[f]quinoxaline-2,3-dione hydrochloride To a dichloromethane (15 mL) solution of 5-(3-tert-butoxycarbonylaminophenyl)-1,4,7,8,9,10-hexahydrobenzo[f]quinoxaline-2,3-dione (180 mg, 0.440 mmol) was added dropwise a dichloromethane (3 mL) solution of trifluoroacetic acid (2 mL) under cooling in an ice-bath. The mixture was stirred for one hour under cooling in ice-bath. The solvent was removed by evaporation under reduced pressure. The obtained solid was washed with ethyl acetate and water, and dried to obtain 4-(3-aminophenyl)-1,4,7,8,9,10-hexahydrobenzo[f]quinoxaline-2,3-dione (93 mg). The obtained compound was dissolved in dichloromethane (5 mL) and methanol (2 mL). To the solution, a 2M hydrogen chloride/methanol solution (0.15 mL) was added. The solvent was removed by evaporation under reduced pressure. To the obtained residue was added ethyl acetate, and the mixture was stirred at room temperature for 18 hours, filtered, and dried to obtain the titled compound as a white crystal (80 mg, yield 77%).
¹H NMR (DMSO-d₆, 400 MHz) δ: 1.6-1.9 (4H, m), 2.6-2.8 (4H, m), 6.20 (1H, d, J=8 Hz), 6.6-6.7 (2H, m), 6.75 (1H, d, J=8 Hz), 6.91 (1H, d, J=7 Hz), 7.35 (1H, t, J=8 Hz), 11.14 (1H, br s).
IR (cm⁻¹, KBr): 3462, 3369, 3224, 2935, 2864, 1705, 1685, 1631, 1604, 1493, 1402, 1279, 1252, 995, 781, 690.
FAB-MS (m/z): 308 (M+1: free base).

Example 8

4-(1H-Indol-4-yl)-1,4,7,8,9,10-hexahydrobenzo[f]quinoxaline-2,3-dione (1) 1-Nitro-2-[1-[2-(trimethylsilyl)ethoxymethyl]-1H-indol-4-yl]amino-5,6,7,8-tetrahydronaphthalene 1-Nitro-5,6,7,8-tetrahydronaphthalen-2-yl triflate and 4-amino-1-[2-(trimethylsilyl)ethoxymethyl]-1H-indole were used in a process similar to Example 1(1) to give the titled compound.
¹H NMR (CDCl₃, 400 MHz) δ: -0.05 (9H, s), 0.89 (2H, t, J=8 Hz), 1.7-1.9 (4H, m), 2.6-2.9 (4H, m), 3.49 (2H, t, J=8 Hz), 5.47 (2H, s), 6.39 (1H, d, J=3 Hz), 6.9-7.3 (6H, m), 7.59 (1H, br s).

(2) 1-Amino-2-[1-[2-(trimethylsilyl)ethoxymethyl]-1H-indol-4-yl]amino-5,6,7,8-tetrahydronaphthalene 1-Nitro-2-[1-[2-(trimethylsilyl)ethoxymethyl]-1H-indol-4-yl]amino-5,6,7,8-tetrahydronaphthalene was used in a process similar to Example 1(2) to give the titled compound.
¹H NMR (CDCl₃, 400 MHz) δ: -0.04 (9H, s), 0.90 (2H, t, J=8 Hz), 1.7-2.0 (4H, m), 2.5-2.6 (2H, m), 2.7-2.8 (2H, m), 3.50 (2H, t, J=8 Hz), 3.83 (2H, br s), 5.35 (1H, br s), 5.45 (2H, s), 6.26 (1H, d, J=7 Hz), 6.47 (1H, d, J=3 Hz), 6.54 (1H, d, J=8 Hz), 6.9-7.1 (3H, m), 7.10 (1H, d, J=3 Hz).

(3) 4-[1-[2-(Trimethylsilyl)ethoxymethyl]-1H-indol-4-yl]-1,4,7,8,9,10-hexahydrobenzo[f]quinoxaline-2,3-dione 1-Amino-2-[1-[2-(trimethylsilyl)ethoxymethyl]-1H-indol-4-yl]amino-5,6,7,8-tetrahydronaphthalene and oxalyl chloride were used in a process similar to Example 1(3) to give the titled compound.
¹H NMR (CDCl₃, 400 MHz) δ: -0.04 (9H, s), 0.8-1.0 (2H, m), 1.7-2.0 (4H, m), 2.7-2.8 (4H, m), 3.4-3.6 (2H, m), 5.49 (1H, d, J=11 Hz), 5.54 (1H, d, J=11 Hz), 6.18 (1H, m), 6.25 (1H, d, J=8 Hz), 6.67 (1H, d, J=9 Hz), 7.09 (1H, d, J=8 Hz), 7.17 (1H, d, J=3 Hz), 7.40 (1H, d, J=8 Hz), 7.64 (1H, d, J=8 Hz), 8.92 (1H, br s).

(4) 4-(1H-Indol-4-yl)-1,4,7,8,9,10-hexahydrobenzo[f]quinoxaline-2,3-dione

A mixture of 4-[1-[2-(trimethylsilyl)ethoxymethyl]-1H-indol-4-yl]-1,4,7,8,9,10-hexahydrobenzo[f]quinoxaline-2,3-dione (180 mg, 0.400 mmol), a 1M tetrabutylammonium fluoride/tetrahydrofuran solution (4 mL, 4.00 mmol), and ethylenediamine (260 μL, 4.00 mmol) was refluxed for 18 hours. The solvent was removed by evaporation under reduced pressure. To the obtained residue was added a dilute hydrochloric acid aqueous solution. The mixture was stirred at room temperature for 18 hours. The precipitate was collected by filtration, washed with water, and dried to obtain the titled compound (85 mg, yield 66%).
¹H NMR (DMSO-d₆, 400 MHz) δ: 1.6-1.9 (4H, m), 2.6-2.7 (2H, m), 2.7-2.9 (2H, m), 6.02 (1H, d, J=9 Hz), 6.13 (1H, s), 6.64 (1H, d, J=8 Hz), 6.96 (1H, d, J=7 Hz), 7.26 (1H, t, J=8 Hz), 7.35 (1H, t, J=3 Hz), 7.57 (1H, d, J=8 Hz), 11.17 (1H, br s), 11.40 (1H, br s).
IR (cm⁻¹, KBr): 3373, 3221, 3172, 3072, 2941, 2856, 1711, 1674, 1618, 1498, 1439, 1394, 1344, 1300, 1267, 1248, 1205, 1155, 1095, 897, 833, 806, 752, 698, 577.
FAB-MS (m/z): 332 (M+1).

Example 9

N-[3-(2,3-Dioxo-2,3,7,8,9,10-hexahydrobenzo[f]quinoxalin-4(1H)-yl)phenyl]-2-nitrobenzenesulfonamide A mixture of 4-(3-aminophenyl)-1,4,7,8,9,10-hexahydrobenzo[f]quinoxaline-2,3-dione (228 mg, 0.74 mmol), 2-nitrobenzenesulfonyl chloride (247 mg, 1.11 mmol), and dry pyridine (5 mL) was refluxed at 80° C. for 4 hours. After cooling on standing, the solvent was removed by evaporation under reduced pressure. The obtained residue was extracted with chloroform, washed with water and a dilute hydrochloric acid aqueous solution, and dried over anhydrous sodium sulfate. The solvent was removed by evaporation under reduced pressure. The obtained residue was purified by silica gel column chromatography (chloroform/methanol=100/1) to obtain the titled compound as a brown crystal (365 mg, yield 100%).

$^1$H NMR (CDCl$_3$, 400 MHz) δ: 1.7-1.9 (2H, m), 1.9-2.0 (2H, m), 2.6-2.8 (4H, m), 6.18 (1H, d, J=8 Hz), 6.75 (1H, d, J=9 Hz), 7.08 (1H, d, J=8 Hz), 7.2-7.4 (2H, m), 7.49 (1H, t, J=8 Hz), 7.53 (1H, br s), 7.6-7.8 (2H, m), 7.81 (1H, dd, J=2 Hz, 7 Hz), 7.92 (1H, dd, J=2 Hz, 7 Hz), 8.92 (1H, br s).

IR (cm$^{-1}$, KBr): 2933, 1697, 1595, 1541, 1491, 1439, 1362, 1306, 1169, 1126.

FAB-MS (m/z): 493 (M+1).

Example 10

4-(3-Methylaminophenyl)-1,4,7,8,9,10-hexahydrobenzo[f]quinoxaline-2,3-dione hydrochloride (1) N-[3-(2,3-Dioxo-2,3,7,8,9,10-hexahydrobenzo[f]quinoxalin-4(1H)-yl)phenyl]-N-methyl-2-nitrobenzenesulfonamide and N-methyl-N-[3-(1-methyl-2,3-dioxo-2,3,7,8,9,10-hexahydrobenzo[f]quinoxalin-4(1H)-yl)phenyl]-2-nitrobenzenesulfonamide A mixture of N-[3-(2,3-dioxo-2,3,7,8,9,10-hexahydrobenzo[f]quinoxalin-4(1H)-yl)phenyl]-2-nitrobenzenesulfonamide (100 mg, 0.203 mmol), methyl iodide (35 mg, 0.244 mmol), potassium carbonate (30.9 mg, 0.223 mmol), and dry DMF (2 mL) was stirred at room temperature for 18 hours. To the reaction solution were added ice-cold water and a saturated aqueous sodium hydrogen carbonate solution. The precipitated crystal was collected by filtration, washed with water, and dried. The obtained crude compound was subjected to silica gel column chromatography (chloroform) to obtain N-methyl-N-[3-(1-methyl-2,3-dioxo-2,3,7,8,9,10-hexahydrobenzo[f]quinoxalin-4(1H)-yl)phenyl]-2-nitrobenzenesulfonamide (70 mg, yield 66%) from the formerly eluted fraction.

$^1$H NMR (CDCl$_3$, 400 MHz) δ: 1.7-2.0 (4H, m), 2.7-2.9 (2H, m), 3.1-3.2 (2H, m), 3.42 (3H, s), 4.11 (3H, s), 6.30 (1H, d, J=9 Hz), 6.93 (1H, d, J=9 Hz), 7.1-7.3 (2H, m), 7.4-7.7 (6H, m).

In the above mentioned column chromatography, N-[3-(2,3-dioxo-2,3,7,8,9,10-hexahydrobenzo[f]quinoxalin-4(1H)-yl)phenyl]-N-methyl-2-nitrobenzenesulfonamide (39 mg, yield 38%) was further obtained from the latterly eluted fraction.

$^1$H NMR (CDCl$_3$, 400 MHz) δ: 1.7-1.8 (2H, m), 1.8-1.9 (2H, m), 2.7-2.9 (4H, m), 3.41 (3H, s), 6.29 (1H, d, J=8 Hz), 6.77 (1H, d, J=8 Hz), 7.20 (1H, t, J=2 Hz), 7.2-7.3 (1H, m), 7.4-7.7 (6H, m), 9.45 (1H, br s).

(2) 4-(3-Methylaminophenyl)-1,4,7,8,9,10-hexahydrobenzo[f]quinoxaline-2,3-dione hydrochloride A mixture of N-[3-(2,3-dioxo-2,3,7,8,9,10-hexahydrobenzo[f]quinoxalin-4(1H)-yl)phenyl]-N-methyl-2-nitrobenzenesulfonamide (35 mg, 0.070 mmol), thiophenol (8.5 μL, 0.083 mmol), potassium carbonate (29 mg, 0.210 mmol), and dry DMF (1 mL) was stirred at room temperature for 18 hours. To the reaction solution was added ice-cold water. The precipitated crystal was collected by filtration, washed with water, and dried. The obtained crude compound was suspended in a methanol (1 mL) and 2M hydrogen chloride/methanol solution (40 μL). To the suspension was added chloroform to form a solution. The solvent was removed by evaporation under reduced pressure. To the obtained residue was added water, and concentrated again to obtain the titled compound as a pale yellow crystal (15 mg, yield 71%).

$^1$H NMR (DMSO-d$_6$, 400 MHz) δ: 1.6-1.9 (4H, m), 2.6-2.8 (4H, m), 2.71 (3H, s), 6.21 (1H, d, J=8 Hz), 6.5-6.7 (2H, m), 6.74 (1H, d, J=8 Hz), 6.83 (1H, d, J=8 Hz), 7.35 (1H, t, J=8 Hz), 11.13 (1H, br s).

IR (cm$^{-1}$, KBr): 3379, 3238, 2931, 1708, 1670, 1610, 1394, 1342, 1307, 1269.

FAB-MS (m/z): 322 (M+1: free base).

Example 11

1-Methyl-4-(3-methylaminophenyl)-1,4,7,8,9,10-hexahydrobenzo[f]quinoxaline-2,3-dione hydrochloride N-Methyl-N-[3-(1-methyl-2,3-dioxo-2,3,7,8,9,10-hexahydrobenzo[f]quinoxalin-4(1H)-yl)phenyl]-2-nitrobenzenesulfonamide was used in a process similar to Example 10(2) to give the titled compound.

$^1$H NMR (DMSO-d$_6$, 400 MHz) δ: 1.7-1.9 (4H, m), 2.68 (3H, S), 2.7-2.8 (2H, m), 3.0-3.1 (2H, m), 4.01 (3H, s), 6.34 (1H, d, J=8 Hz), 6.4-6.5 (2H, m), 6.74 (1H, d, J=7 Hz), 6.98 (1H, d, J=9 Hz), 7.32 (1H, t, J=8 Hz).

IR (cm$^{-1}$, KBr): 3361, 2933, 1676, 1608, 1487, 1244, 1215, 793, 727, 687.

FAB-MS (m/z): 336 (M+1: free base).

Example 12

4-(3-Fluorophenyl)-1,4-dihydrobenzo[f]quinoxaline-2,3-dione (1) N-(3-Fluorophenyl)-1-nitronaphthalene-2-amine 1-Nitro-2-naphthyl triflate and 3-fluoroaniline were used in a process similar to Example 1(1) to give the titled compound.

$^1$H NMR (CDCl$_3$, 400 MHz) δ: 6.91 (1H, dt, J=2 Hz, 8 Hz), 6.98 (1H, dt, J=2 Hz, 10 Hz), 7.03 (1H, dd, J=2 Hz, 8 Hz), 7.3-7.5 (3H, m), 7.63 (1H, ddd, J=1 Hz, 7 Hz, 8 Hz), 7.73 (1H, d, J=8 Hz), 7.79 (1H, d, J=9 Hz), 8.44 (1H, d, J=9 Hz), 9.20 (1H, br s).

(2) N$^2$-(3-Fluorophenyl)naphthalene-1,2-diamine

N-(3-Fluorophenyl)-1-nitronaphthalene-2-amine was used in a process similar to Example 1(2) to give the titled compound.

$^1$H NMR (CDCl$_3$, 400 MHz) δ: 4.0-4.6 (2H, br s), 5.2-5.5 (1H, br s), 6.33 (1H, dt, J=2 Hz, 9 Hz), 6.4-6.5 (2H, m), 7.0-7.2 (1H, m), 7.23 (1H, d, J=9 Hz), 7.30 (1H, d, J=8 Hz), 7.4-7.5 (2H, m), 7.7-7.9 (2H, m).

(3) 4-(3-Fluorophenyl)-1,4-dihydrobenzo[f]quinoxaline-2,3-dione

N$^2$-(3-Fluorophenyl)naphthalene-1,2-diamine was used in a process similar to Example 1(3) to give the titled compound.

$^1$H NMR (CDCl$_3$, 400 MHz) δ: 6.61 (1H, d, J=9 Hz), 7.32 (1H, d, J=8 Hz), 7.3-7.7 (5H, m), 7.71 (1H, q, J=8 Hz), 7.90 (1H, d, J=7 Hz), 8.67 (1H, d, J=8 Hz), 12.34 (1H, br s).

FAB-MS (m/z): 307 (M+1).

Example 13

4-(3-Aminophenyl)-1,4-dihydrobenzo[f]quinoxaline-2,3-dione hydrochloride

(1) 1-Nitro-2-(3-tertbutoxycarbonylaminophenyl)aminonaphthalene

1-Nitronaphthalen-2-yl triflate (5.94 g, 18.5 mmol) and tert-butyl 3-aminophenylcarbamate were used in a process similar to Example 1(1) to give the titled compound (4.83 g, yield 69%).

(2) 1-Amino-2-(3-tertbutoxycarbonylaminophenyl)aminonaphthalene

1-Nitro-2-(3-tertbutoxycarbonylaminophenyl)aminonaphthalene (4.83 g, 12.7 mmol) was used in a process similar to Example 1(2) to give the titled compound (12.6 g, yield 99%).

(3) 4-(3-tert-Butoxycarbonylaminophenyl)-1,4-dihydrobenzo[f]quinoxaline-2,3-dione 1-Amino-2-(3-tertbutoxycarbonylaminophenyl)aminonaphthalene (1.05 g, 3 mmol) and oxalyl chloride were used in a process similar to Example 1(3) to give the titled compound (0.50 g, yield 41%).

(4) 4-(3-Aminophenyl)-1,4-dihydrobenzo[f]quinoxaline-2,3-dione hydrochloride 4-(3-tert-Butoxycarbonylaminophenyl)-1,4-dihydrobenzo[f]quinoxaline-2,3-dione (40 mg, 0.1 mmol) was used in a process similar to Example 7(4) to give the titled compound as a brown powder (33 mg, yield 97%).
$^1$H NMR (DMSO-$d_6$, 400 MHz) δ: 6.69 (1H, d, J=9 Hz), 6.7-6.8 (2H, m), 6.95 (1H, d, J=7 Hz), 7.39 (1H, t, J=8 Hz), 7.52 (1H, t, J=8 Hz), 7.5-7.7 (2H, m), 7.90 (1H, d, J=8 Hz), 8.67 (1H, d, J=8 Hz), 12.30 (1H, s)

Example 14

4-[3-[(2-Iodophenylacetyl)amino]phenyl)-1,4-dihydrobenzo[f]quinoxaline-2,3-dione

4-(3-Aminophenyl)-1,4-dihydrobenzo[f]quinoxaline-2,3-dione (30 mg, 0.1 mmol) and 2-iodophenylacetylchloride were used in a process similar to Example 9 to give the titled compound as a yellow crystal (6 mg, yield 11%).
$^1$H NMR (DMSO-$d_6$, 400 MHz) δ: 3.87 (2H, s), 6.65 (1H, d, J=9 Hz), 6.9-7.1 (1H, m), 7.12 (1H, d, J=8 Hz), 7.3-7.5 (2H, m), 7.5-7.7 (4H, m), 7.7-7.8 (2H, m), 7.84 (1H, d, J=9 Hz), 7.90 (1H, d, J=7 Hz), 8.67 (1H, d, J=9 Hz), 10.52 (1H, s), 12.31 (1H, br s).

Example 15

4-[3-(5-Methyl-[1,3,4]oxadiazol-2-yl)phenyl]-1,4-dihydrobenzo[f]quinoxaline-2,3-dione

(1) 1-Nitro-2-[3-(5-methyl-[1,3,4]oxadiazol-2-yl)phenyl]aminonaphthalene

1-Nitronaphthalen-2-yl triflate (1.54 g, 4.8 mmol) and 3-(5-methyl-[1,3,4]oxadiazol-2-yl)aniline (0.84 g, 4.8 mmol) were used in a process similar to Example 1(1) to give the titled compound (1.17 g, yield 71%).
$^1$H NMR (CDCl$_3$, 400 MHz) δ: 2.62 (3H, s), 7.4-7.5 (5H, m), 7.5-7.6 (2H, m), 7.6-7.7 (3H, m), 7.75 (1H, d, J=8 Hz), 7.82 (1H, d, J=9 Hz), 7.87 (1H, d, J=7 Hz), 7.9-8.0 (1H, m), 8.46 (1H, d, J=9 Hz), 9.28 (1H, s).

(2) 1-Amino-2-[3-(5-methyl-[1,3,4]oxadiazol-2-yl)phenyl]aminonaphthalene

1-Nitro-2-[3-(5-methyl-[1,3,4]oxadiazol-2-yl)phenyl]aminonaphthalene (1.17 g, 3.4 mmol) was used in a process similar to Example 1(2) to give the titled compound (0.54 g, yield 50%).
$^1$H NMR (DMSO-$d_6$, 400 MHz) δ: 2.52 (3H, s), 5.40 (2H, 5), 6.8-6.9 (1H, m), 7.1-7.3 (4H, m), 7.31 (1H, t, J=8 Hz), 7.3-7.5 (2H, m), 7.71 (1H, s), 7.7-7.8 (1H, m), 8.1-8.2 (1H, m)).

(3) 4-[3-(5-Methyl-[1,3,4]oxadiazol-2-yl)phenyl]-1,4-dihydrobenzo[f]quinoxaline-2,3-dione 1-Amino-2-[3-(5-methyl-[1,3,4]oxadiazol-2-yl)phenyl]aminonaphthalene (95 mg, 0.3 mmol) and oxalyl chloride were used in a process similar to Example 1(3) to give the titled compound as white crystal (43 mg, yield 40%).
$^1$H NMR (DMSO-$d_6$, 400 MHz) δ: 2.58 (3H, s), 6.63 (1H, d, J=9 Hz), 7.52 (1H, t, J=8 Hz), 7.57 (1H, d, J=9 Hz), 7.63 (1H, t, J=8 Hz), 7.71 (1H, d, J=8 Hz), 7.8-8.0 (2H, m), 8.10 (1H, s), 8.19 (1H, d, J=8 Hz), 8.69 (1H, d, J=8 Hz), 12.33 (1H, br s).

Example 16

4-[3-(3-Methyl-[1,2,4]oxadiazol-5-yl)phenyl]-1,4-dihydrobenzo[f]quinoxaline-2,3-dione

(1) 1-Nitro-2-[3-(3-methyl-[1,2,4]oxadiazol-5-yl)phenyl]aminonaphthalene

1-Nitronaphthalen-2-yl triflate and 3-(3-methyl-[1,2,4]oxadiazol-5-yl)aniline were used in a process similar to Example 1(1) to give the titled compound.
$^1$H NMR (CDCl$_3$, 400 MHz) δ: 2.47 (3H, s), 7.4-7.5 (3H, m), 7.57 (1H, t, J=8 Hz), 7.65 (1H, dt, J=6 Hz, 2 Hz), 7.76 (1H, d, J=8 Hz), 7.83 (1H, d, J=9 Hz), 7.94 (1H, d, J=8 Hz), 8.02 (1H, br s), 8.45 (1H, d, J=9 Hz), 9.24 (1H, br s).

(2) 1-Amino-2-[3-(3-methyl-[1,2,4]oxadiazol-5-yl)phenyl]aminonaphthalene

1-Nitro-2-[3-(3-methyl-[1,2,4]oxadiazol-5-yl)phenyl]aminonaphthalene was used in a process similar to Example 1(2) to give the titled compound.
$^1$H NMR (CDCl$_3$, 400 MHz) δ: 2.44 (3H, s), 4.41 (2H, br s), 5.45 (1H, br s), 6.85 (1H, ddd, J=1 Hz, 2 Hz, 8 Hz), 7.2-7.4 (3H, m), 7.4-7.6 (4H, m), 7.8-7.9 (2H, m).

(3) 4-[3-(3-Methyl-[1,2,4]oxadiazol-5-yl)phenyl]-1,4-dihydrobenzo[f]quinoxaline-2,3-dione 1-Amino-2-[3-(3-methyl-[1,2,4]oxadiazol-5-yl)phenyl]aminonaphthalene and oxalyl chloride were used in a process similar to Example 1(3) to give the titled compound.
$^1$H NMR (DMSO-$d_6$, 400 MHz) δ: 2.42 (3H, s), 6.63 (1H, d, J=9 Hz), 7.5-7.7 (3H, m), 7.79 (1H, d, J=8 Hz), 7.8-8.0 (2H, m), 8.22 (1H, s), 8.29 (1H, d, J=8 Hz), 8.68 (1H, d, J=8 Hz), 12.33 (1H, br s).

Example 17

4-(4-Hydroxyphenyl)-1,4-dihydrobenzo[f]quinoxaline-2,3-dione sodium salt

(1) 4-(4-Methoxyphenyl)-1,4-dihydrobenzo[f]quinoxaline-2,3-dione

To an anhydrous tetrahydrofuran (5 mL) solution of oxalyl chloride (0.12 mL) was added dropwise an anhydrous tetrahydrofuran (10 mL) solution of $N^2$-(4-methoxyphenyl)naphthalene-1,2-diamine (322 mg, 1.22 mmol) under cooling in an ice-bat. The mixture was stirred under cooling in ice-bath for 30 minutes and at room temperature for one hour. The reaction mixture was poured into a saturated aqueous sodium hydrogen carbonate solution, and extracted with ethyl acetate. The organic layer was dried over anhydrous sodium sulfate. The solvent was removed by evaporation under reduced pressure. The obtained solid was filtered. The crude crystal was washed with ethyl acetate and hexane to obtain the titled compound as a slightly off-white crystal (220 mg, yield 56%).

(2) 4-(4-Hydroxyphenyl)-1,4-dihydrobenzo[f]quinoxaline-2,3-dione

To an anhydrous dichloromethane (8 mL) suspension of 4-(4-methoxyphenyl)-1,4-dihydrobenzo[f]quinoxaline-2,3-dione (200 mg, 0.63 mmol) was added a 1M boron tribromide/dichloromethane solution (0.94 mL, 0.94 mmol) under cooling in an ice-bath. The mixture was stirred at room temperature for 18 hours. The reaction mixture was poured into a saturated aqueous sodium hydrogen carbonate solution. The precipitated solid was washed with water and ethanol. The solid was further washed with hexane, and dried to obtain the titled compound as a off-white crystal (285 mg, yield 45%).
$^1$H NMR (DMSO-d$_6$, 400 MHz) δ: 6.66 (1H, d, J=8 Hz), 6.98 (2H, d, J=7 Hz), 7.19 (2H, d, J=7 Hz), 7.50 (1H, t, J=8 Hz), 7.58 (1H, t, J=7 Hz), 7.89 (1H, d, J=8 Hz), 8.65 (1H, d, J=8 Hz), 9.86 (1H, s), 12.27 (1H, br s).

(3) 4-(4-Hydroxyphenyl)-1,4-dihydrobenzo[f]quinoxaline-2,3-dione sodium salt 4-(4-Hydroxyphenyl)-1,4-dihydrobenzo[f]quinoxaline-2,3-dione (31 mg, 0.102 mmol) was used in a process similar to Example 4(2) to give the titled compound as a gray crystal (25 mg, yield 75%).
$^1$H NMR (DMSO-d$_6$, 400 MHz) δ: 6.55 (1H, d, J=9 Hz), 6.95 (2H, d, J=8 Hz), 7.08 (2H, d, J=8 Hz), 7.25 (1H, d, J=9 Hz), 7.37 (1H, t, J=8 Hz), 7.45 (1H, t, J=8 Hz), 7.73 (1H, d, J=8 Hz), 8.70 (1H, d, J=8 Hz).

Example 18

4-(4-Aminophenyl)-1,4-dihydrobenzo[f]quinoxaline-2,3-dione hydrochloride

(1) 1-Nitro-2-(4-tertbutoxycarbonylaminophenyl)aminonaphthalene

1-Nitronaphthalen-2-yl triflate (2.50 g, 7.78 mmol) and tert-butyl 4-aminophenylcarbamate (1.62 g, 7.78 mmol) were used in a process similar to Example 1(1) to give the titled compound (2.39 g, yield 81%).
$^1$H NMR (CDCl$_3$, 400 MHz) δ: 1.54 (9H, s), 6.52 (1H, br s), 7.21 (3H, d, J=9 Hz), 7.3-7.4 (1H, m), 7.44 (2H, d, J=9 Hz), 7.5-7.7 (1H, m), 7.6-7.8 (2H, m), 8.62 (1H, d, J=9 Hz), 9.68 (1H, br s).

(2) 1-Amino-2-(4-tertbutoxycarbonylaminophenyl)aminonaphthalene

1-Nitro-2-(4-tertbutoxycarbonylaminophenyl)aminonaphthalene (2.39 g, 6.30 mmol) was used in a process similar to Example 1(2) to give the titled compound (1.83 g, yield 83%).
$^1$H NMR (CDCl$_3$, 400 MHz) δ: 1.50 (9H, s), 4.34 (2H, br s), 5.16 (1H, br s), 6.26 (1H, br s), 6.66 (2H, d, J=8 Hz), 7.17 (2H, d, J=8 Hz), 7.2-7.3 (2H, m), 7.4-7.5 (2H, m), 7.7-7.9 (2H, m).

(3) 4-(4-tert-Butoxycarbonylaminophenyl)-1,4-dihydrobenzo[f]quinoxaline-2,3-dione 1-Amino-2-(4-tertbutoxycarbonylaminophenyl)aminonaphthalene (700 mg, 2.0 mmol) and oxalyl chloride (330 mg, 2.6 mmol) were used in a process similar to Example 1(3) to give the titled compound (304 mg, yield 38%).

(4) 4-(4-Aminophenyl)-1,4-dihydrobenzo[f]quinoxaline-2,3-dione hydrochloride 4-(4-tert-Butoxycarbonylaminophenyl)-1,4-dihydrobenzo[f]quinoxaline-2,3-dione (300 mg, 0.74 mmol) was used in a process similar to Example 7(4) to give the titled compound (212 mg, yield 90%) as a pale gray solid.
$^1$H NMR (DMSO-d$_6$, 400 MHz) δ: 6.70 (1H, d, J=9 Hz), 6.99 (2H, d, J=8 Hz), 7.16 (2H, d, J=9 Hz), 7.51 (1H, t, J=8 Hz), 7.5-7.7 (2H, m), 7.90 (1H, d, J=8 Hz), 8.66 (1H, d, J=8 Hz), 12.30 (1H, br s).

Example 19

N-[4-(2,3-Dioxo-2,3-dihydrobenzo[f]quinoxalin-4(1H)-yl)phenyl]-2-nitrobenzenesulfonamide 4-(4-Aminophenyl)-1,4-dihydrobenzo[f]quinoxaline-2,3-dione hydrochloride (80 mg, 0.24 mmol) and 2-nitrobenzenesulfonyl chloride (78 mg, 0.35 mmol) were used in a process similar to Example 9 to give the titled compound (53 mg, yield 46%) as a white solid.
$^1$H NMR (DMSO-d$_6$, 400 MHz) δ: 6.51 (1H, d, J=9 Hz), 7.35 (4H, s), 7.4-7.7 (3H, m), 7.8-8.0 (3H, m), 8.0-8.1 (1H, m), 8.1-8.2 (1H, m), 8.65 (1H, d, J=9 Hz), 11.07 (1H, br s), 12.30 (1H, br s).

Example 20

4-[4-(5-Methyl-[1,3,4]oxadiazol-2-yl)phenyl]-1,4-dihydrobenzo[f]quinoxaline-2,3-dione

(1) 1-Nitro-2-[4-(5-methyl-[1,3,4]oxadiazol-2-yl)phenyl]aminonaphthalene

1-Nitronaphthalen-2-yl triflate (1.67 g, 5.2 mmol) and 4-(5-methyl-[1,3,4]oxadiazol-2-yl)aniline (0.91 g, 5.2 mmol) were used in a process similar to Example 1(1) to give the titled compound (1.27 g, yield 71%).
$^1$H NMR (CDCl$_3$, 400 MHz) δ: 2.63 (3H, s), 7.35 (2H, d, J=9 Hz), 7.45 (1H, t, J=8 Hz), 7.52 (1H, d, J=8 Hz), 7.65 (1H, t, J=8 Hz), 7.78 (1H, d, J=8 Hz), 7.86 (1H, d, J=9 Hz), 8.04 (2H, d, J=9 Hz), 8.38 (1H, d, J=9 Hz), 9.09 (1H, s).

(2) 1-Amino-2-[4-(5-methyl-[1,3,4]oxadiazol-2-yl) phenyl]aminonaphthalene

1-Nitro-2-[4-(5-methyl-[1,3,4]oxadiazol-2-yl)phenyl] aminonaphthalene (1.26 g, 3.64 mmol) was used in a process similar to Example 1(2) to give the titled compound (1.15 g, yield 100%).
$^1$H NMR (CDCl$_3$, 400 MHz) δ: 2.57 (3H, s), 4.40 (2H, br s), 5.63 (1H, s), 6.75 (2H, d, J=9 Hz), 7.2-7.3 (1H, m), 7.33 (1H, d, J=9 Hz), 7.4-7.6 (2H, m), 7.8-7.9 (4H, m).

(3) 4-[4-(5-Methyl-[1,3,4]oxadiazol-2-yl)phenyl]-1, 4-dihydrobenzo[f]quinoxaline-2,3-dione 1-Amino-2-[4-(5-methyl-[1,3,4]oxadiazol-2-yl)phenyl] aminonaphthalene (190 mg, 0.6 mmol) and oxalyl chloride were used in a process similar to Example 1(3) to give the titled compound (150 mg, yield 68%) as a gray crystal.
$^1$H NMR (DMSO-d$_6$, 400 MHz) δ: 2.64 (3H, 5), 6.58 (1H, d, J=9 Hz), 7.4-7.5 (2H, m), 7.57 (1H, t, J=8 Hz), 7.65 (2H, d, J=8 Hz), 7.84 (1H, d, J=8 Hz), 8.24 (2H, d, J=8 Hz), 8.71 (1H, d, J=9 Hz), 12.24 (1H, br s).

Example 21

4-[3-[(2-Trifluoromethylbenzoyl)aminophenyl)-2,3, 7,8,9,10-hexahydro-1H-benzo[f]quinoxaline-2,3-dione 4-(3-Aminophenyl)-1,4,7,8,9,10-hexahydrobenzo[f]quinoxaline-2,3-dione (22 mg, 0.064 mmol) and 2-trifluoromethylbenzoyl chloride (20 mg, 0.096 mmol) were used in a process similar to Example 9 to give the titled compound (a slightly brown crystal, 15 mg, yield 49%).
$^1$H NMR (DMSO-d$_6$, 400 MHz) δ: 1.6-1.8 (4H, m), 2.6-2.8 (4H, m), 6.17 (1H, d, J=8 Hz), 6.76 (1H, d, J=8 Hz), 7.10 (1H, d, J=8 Hz), 7.59 (1H, t, J=8 Hz), 7.6-7.9 (7H, m), 10.82 (1H, br s), 11.14 (1H, br s).

Example 22

N-[3-(2,3-Dioxo-2,3,7,8,9,10-hexahydro-1H-benzo [f]quinoxalin-4-yl)phenyl]benzenesulfonamide 4-(3-Aminophenyl)-1,4,7,8,9,10-hexahydrobenzo[f]quinoxaline-2,3-dione (50 mg, 0.145 mmol) and benzenesulfonyl chloride (38 mg, 0.218 mmol) were used in a process similar to Example 9 to give the titled compound (a white crystal, 35 mg, yield 54%).
$^1$H NMR (DMSO-d$_6$, 400 MHz) δ: 1.6-1.8 (4H, m), 2.6-2.8 (4H, m), 5.73 (1H, d, J=8 Hz), 6.67 (1H, d, J=8 Hz), 7.00 (1H, d, J=8 Hz), 7.03 (1H, s), 7.23 (1H, d, J=8 Hz), 7.45 (1H, t, J=7 Hz), 7.54 (1H, t, J=7 Hz), 7.63 (1H, t, J=7 Hz), 7.73 (1H, d, J=7 Hz), 10.51 (1H, br s), 11.10 (1H, br s).

Example 23

3-Bromo-N-[3-(2,3-dioxo-2,3,7,8,9,10-hexahydro-1H-benzo[f]quinoxalin-4-yl)phenyl]benzenesulfonamide 4-(3-Aminophenyl)-1,4,7,8,9,10-hexahydrobenzo[f]quinoxaline-2,3-dione (30 mg, 0.097 mmol) and 3-bromobenzenesulfonyl chloride (21 μL, 0.146 mmol) were used in a process similar to Example 9 to give the titled compound (a white crystal, 15 mg, yield 29%).
$^1$H NMR (DMSO-d$_6$, 400 MHz) δ: 1.6-1.8 (4H, m), 2.6-2.8 (4H, m), 5.75 (1H, d, J=8 Hz), 6.69 (1H, d, J=9 Hz), 7.0-7.1 (2H, m), 7.24 (1H, d, J=8 Hz), 7.4-7.6 (2H, m), 7.71 (1H, d, J=8 Hz), 7.81 (1H, s), 7.86 (1H, d, J=8 Hz), 10.61 (1H, br s), 11.11 (1H, br s).

Example 24

N-[3-(2,3-Dioxo-2,3,7,8,9,10-hexahydro-1H-benzo [f]quinoxalin-4-yl)phenyl]-1-naphthalenesulfonamide 4-(3-Aminophenyl)-1,4,7,8,9,10-hexahydrobenzo[f]quinoxaline-2,3-dione (30 mg, 0.097 mmol) and 1-naphthalenesulfonyl chloride (33 mg, 0.146 mmol) were used in a process similar to Example 9 to give the titled compound (a white crystal, 14 mg, yield 29%).
$^1$H NMR (DMSO-d$_6$, 400 MHz) δ: 1.6-1.8 (4H, m), 2.6-2.8 (4H, m), 5.57 (1H, d, J=8 Hz), 6.60 (1H, d, J=8 Hz), 6.88 (1H, d, J=8 Hz), 6.99 (1H, s), 7.12 (1H, d, J=8 Hz), 7.34 (1H, t, J=8 Hz), 7.57 (1H, t, J=8 Hz), 7.6-7.8 (2H, m), 8.07 (1H, d, J=8 Hz), 8.16 (1H, d, J=7 Hz), 8.23 (1H, d, J=8 Hz), 8.70 (1H, d, J=9 Hz), 10.92 (1H, br s), 11.08 (1H, br s).

Example 25

N-[3-(2,3-Dioxo-2,3,7,8,9,10-hexahydro-1H-benzo [f]quinoxalin-4-yl)phenyl]-2-naphthalenesulfonamide 4-(3-Aminophenyl)-1,4,7,8,9,10-hexahydrobenzo[f]quinoxaline-2,3-dione (30 mg, 0.097 mmol) and 2-naphthalenesulfonyl chloride (33 mg, 0.146 mmol) were used in a process similar to Example 9 to give the titled compound (a white crystal, 9 mg, yield 19%).
$^1$H NMR (DMSO-d$_6$, 400 MHz) δ: 1.6-1.8 (4H, m), 2.5-2.8 (4H, m), 5.48 (1H, d, J=9 Hz), 6.13 (1H, d, J=8 Hz), 6.93 (1H, d, J=7 Hz), 7.02 (1H, s), 7.27 (1H, d, J=9 Hz), 7.42 (1H, t, J=8 Hz), 7.64 (1H, t, J=7 Hz), 7.6-7.8 (2H, m), 8.0-8.1 (3H, m), 8.37 (1H, s), 10.62 (1H, br s), 11.07 (1H, br s).

Example 26

N-[3-(2,3-Dioxo-2,3,7,8,9,10-hexahydro-1H-benzo [f]quinoxalin-4-yl)phenyl]-2-thiophenesulfonamide 4-(3-Aminophenyl)-1,4,7,8,9,10-hexahydrobenzo[f]quinoxaline-2,3-dione (30 mg, 0.097 mmol) and 2-thiophenesulfonyl chloride (27 mg, 0.146 mmol) were used in a process similar to Example 9 to give the titled compound (a white crystal, 9 mg, yield 20%).
$^1$H NMR (DMSO-d$_6$, 400 MHz) δ: 1.6-1.8 (4H, m), 2.6-2.8 (4H, m), 5.85 (1H, d, J=8 Hz), 6.72 (1H, d, J=8 Hz), 7.0-7.1 (2H, m), 7.12 (1H, t, J=5 Hz), 7.28 (1H, d, J=9 Hz), 7.4-7.6 (2H, m), 7.93 (1H, d, J=5 Hz), 10.66 (1H, br s), 11.12 (1H, br s).

Example 27

N-[3-(2,3-Dioxo-2,3,7,8,9,10-hexahydro-1H-benzo [f]quinoxalin-4-yl)phenyl]-3-pyridinesulfonamide hydrochloride 4-(3-Aminophenyl)-1,4,7,8,9,10-hexahydrobenzo[f]quinoxaline-2,3-dione (30 mg, 0.097 mmol) and 3-pyridinesulfonyl chloride (26 mg, 0.146 mmol) were used in a process similar to Example 9 to give the titled compound (a white crystal, 12 mg, yield 26%).

$^1$H NMR (DMSO-$d_6$, 400 MHz) δ: 1.6-1.8 (4H, m), 2.6-2.8 (4H, m), 5.74 (1H, d, J=9 Hz), 6.69 (1H, d, J=8 Hz), 7.0-7.1 (2H, m), 7.2-7.3 (1H, m), 7.49 (1H, t, J=8 Hz), 7.61 (1H, dd, J=5 Hz, 9 Hz), 8.10 (1H, dt, J=2 Hz, 8 Hz), 8.81 (1H, dd, J=1 Hz, 5 Hz), 8.86 (1H, d, J=2 Hz), 10.75 (1H, br s), 11.11 (1H, br s).

Example 28

N-[3-(2,3-Dioxo-2,3,7,8,9,10-hexahydro-1H-benzo[f]quinoxalin-4-yl)phenyl]-8-quinolinesulfonamide hydrochloride 4-(3-Aminophenyl)-1,4,7,8,9,10-hexahydrobenzo[f]quinoxaline-2,3-dione (30 mg, 0.097 mmol) and 8-quinolinesulfonyl chloride (33 mg, 0.146 mmol) were used in a process similar to Example 9 to give the titled compound (a pale yellow amorphous, 7 mg, yield 13%).

$^1$H NMR (CD$_3$OD, 400 MHz) δ: 1.7-2.0 (4H, m), 2.7-2.9 (4H, m), 5.78 (1H, d, J=8 Hz), 6.68 (1H, d, J=9 Hz), 6.96 (1H, d, J=7 Hz), 7.1-7.2 (2H, m), 7.33 (1H, t, J=8 Hz), 7.7-7.9 (2H, m), 8.37 (1H, d, J=8 Hz), 8.47 (1H, d, J=7 Hz), 8.75 (1H, d, J=8 Hz), 9.15 (1H, s).

Example 29

4-[3-(1H-Tetrazol-1-yl)phenyl]-2,3,7,8,9,10-tetrahydro-1H-benzo[f]quinoxaline-2,3-dione A mixture of 4-(3-aminophenyl)-1,4,7,8,9,10-hexahydrobenzo[f]quinoxaline-2,3-dione (32 mg, 0.103 mmol), sodium azide (33 mg, 0.515 mmol), triethyl orthoformate (0.1 mL, and acetic acid (0.2 mL) was refluxed at 80° C. for 2 hours. After cooling on standing, water was added to the reaction solution. The precipitated crystal was collected by filtration. The obtained crystal was washed with hexane and water to obtain the titled compound (a slightly brown crystal, 20 mg, yield 53%).

$^1$H NMR (CD$_3$OD, 400 MHz) δ: 1.6-1.9 (4H, m), 2.6-2.9 (4H, m), 6.20 (1H, d, J=9 Hz), 6.75 (1H, d, J=8 Hz), 7.59 (1H, d, J=8 Hz), 7.8-8.0 (1H, m), 8.04 (1H, s), 8.12 (1H, d, J=6 Hz), 10.12 (1H, s), 11.19 (1H, br s).

Example 30

Experimental Procedure

P2X$_4$ receptor antagonism of the compound of the present invention was measured as described below.

1321N1 cells stably expressing human P2X$_4$ receptors were plated in 96-well assay plate and cultured 24 hours at 37° C. in an atmosphere of 5% CO$_2$ for intracellular calcium assay. Fura-2 AM calcium fluorescent indicator was used for the intracellular calcium assay. Fura-2 AM was dissolved in an assay buffer, and the solution was loaded onto cells. The obtained plate was used for fluorescent assay. Test compounds were treated to cells 15 minutes before the addition of ATP, and the response to intracellular calcium influx induced by addition of ATP was monitored by a micro plate reader. The fluorescence ratio of excitations wavelengths of 340 nm and 380 nm was used as the index of intracellular calcium change. The inhibition activities of the test compounds were calculated by comparison with the absence of the test compound (control).

The results are set forth in Table 25.

(Experimental Results)

TABLE 25

| Example No. | IC$_{50}$ (μM) |
|---|---|
| Example 2 | 0.46 |
| Example 3 | 6.6 |
| Example 7 | 5.1 |
| Example 9 | 2.1 |

As is evident from Table 25, the compounds of the present invention described in Examples have excellent P2X$_4$ receptor antagonism.

Example 31

P2X$_4$ receptor antagonism of the compound of the present invention was measured in the same manner as in Example 30. The results are set forth in Table 26.

TABLE 26

| Example No. | IC$_{50}$ (μM) |
|---|---|
| Example 13 | 2.1 |
| Example 14 | 0.88 |
| Example 15 | 6.7 |
| Example 17 | 2.7 |
| Example 18 | 5.7 |
| Example 21 | 7.7 |
| Example 22 | 0.8 |
| Example 23 | 1.3 |
| Example 24 | 2.6 |
| Example 26 | 1.8 |
| Example 27 | 3.0 |
| Example 28 | 1.9 |

As is evident from Table 26, the compounds of the present invention have excellent P2X$_4$ receptor antagonism.

The invention claimed is:

1. A compound having the following formula (I) or a pharmacologically acceptable salt thereof:

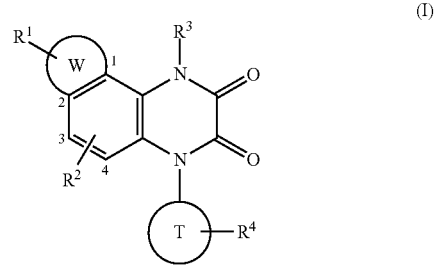

wherein each of R$^1$ and R$^2$ independently is hydrogen, a C$_{1-8}$ alkyl group, a C$_{2-8}$ alkenyl group, a C$_{1-8}$ alkoxy group, a C$_{1-8}$ alkyl group having one to three halogen atoms, a C$_{1-8}$ alkoxy group having one to three halogen atoms, an aralkyl group consisting of a C$_{6-10}$ aryl moiety and a C$_{1-3}$ alkylene moiety, a halogen atom, hydroxyl, nitro, cyano, amino, a C$_{1-8}$ alkylamino group, a C$_{2-8}$ dialkylamino group, a C$_{2-8}$ acylamino group, a C$_{2-8}$ acylamino group having one to three halogen atoms, a C$_{1-8}$ alkylsulfonylamino group, carboxyl, a C$_{2-8}$ acyl group, an alkoxycarbonyl group comprising a C$_{1-8}$ alkoxy moiety, carbamoyl, a $C_{1-8}$ alkylthio group, a $C_{1-8}$ alkylsulfinyl group, a $C_{1-8}$ alkylsulfonyl group, or sulfamoyl;

$R^3$ is hydrogen, a $C_{1-8}$ alkyl group, a $C_{2-8}$ alkenyl group, a $C_{1-8}$ alkyl group having one to three halogen atoms, or an aralkyl group consisting of a $C_{6-10}$ aryl moiety and a $C_{1-3}$ alkylene moiety;

$R^4$ is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, an aralkyl group consisting of a $C_{6-10}$ aryl moiety and a $C_{1-3}$ alkylene moiety, a $C_{1-8}$ alkyl group having hydroxyl, a halogen atom, hydroxyl, nitro, cyano, amino, a $C_{1-8}$ alkylamino group, a $C_{1-5}$ alkylamino group having one to five halogen atoms, a $C_{2-8}$ dialkylamino group, a $C_{2-8}$ acylamino group, a $C_{2-8}$ acylamino group having one to three halogen atoms, a $C_{1-8}$ alkylsulfonylamino group, benzenesulfonylamino optionally having one or more substituents, carboxyl, a acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, sulfamoyl, phenyl optionally having one or more substituents, or a heterocyclic group optionally having one or more substituents;

the ring shown below is a five-membered to eight-membered ring optionally comprising one or more heteroatoms selected from N, S, and O as the members of the ring, and being condensed with the benzene ring at the positions of 1 and 2 of the benzene ring; and

the ring shown below is an aromatic ring selected from the group consisting of benzene ring, naphthalene ring, pyridine ring, pyrimidine ring, quinoline ring, indole ring, indoline ring, benzimidazole ring, indazole ring, benzisoxazole ring, and benzotriazole ring.

2. A compound or a pharmacologically acceptable salt thereof defined in claim 1, wherein each of $R^1$ and $R^2$ independently is hydrogen, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, or amino.

3. A compound or a pharmacologically acceptable salt thereof defined in claim 1, wherein $R^3$ is hydrogen or a $C_{1-8}$ alkyl group.

4. A compound or a pharmacologically acceptable salt thereof defined in claim 1, wherein $R^4$ is hydrogen, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a $C_{1-8}$ alkyl group having hydroxyl, a halogen atom, hydroxyl, cyano, amino, a $C_{1-8}$ alkylamino group, a $C_{2-8}$ dialkylamino group, a $C_{1-8}$ alkylsulfonylamino group, benzenesulfonylamino optionally having one or more substituents, phenyl optionally having one or more substituents, or a heterocyclic group optionally having one or more substituents.

5. A compound or a pharmacologically acceptable salt thereof defined in claim 1, wherein $R^4$ is a heterocyclic group optionally having one or more substituents, said heterocyclic group being tetrazolyl, triazolyl, pyridyl, imidazolyl, oxazolyl, or thiazolyl, and said substituents being selected from the group consisting of a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, and a $C_{2-8}$ dialkylamino group.

6. A compound or a pharmacologically acceptable salt thereof defined in claim 1, wherein $R^4$ is hydrogen, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, cyano, amino, a $C_{1-8}$ alkylamino group, a $C_{2-8}$ dialkylamino group, or benzenesulfonylamino optionally having one or more substituents, said substituents being selected from the group consisting of a $C_{1-8}$ alkyl group, a $C_{1-8}$ alkoxy group, a halogen atom, and nitro.

7. A compound or a pharmacologically acceptable salt thereof defined in claim 1, wherein the ring shown below is naphthalene ring, tetrahydronaphthalene ring, or indan ring.

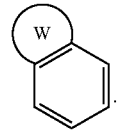

8. A compound or a pharmacologically acceptable salt thereof defined in claim 1, wherein the ring shown below is benzene ring or indole ring.

9. A compound having the following formula (II) or a pharmacologically acceptable salt thereof:

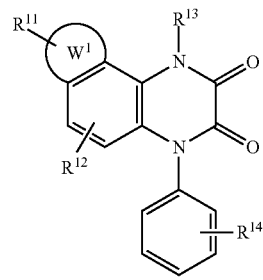

(II)

wherein each of $R^{11}$ and $R^{12}$ independently is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, an aralkyl group consisting of a $C_{6-10}$ aryl moiety and a $C_{1-3}$ alkylene moiety, a halogen atom, hydroxyl, nitro, cyano, amino, a $C_{1-8}$ alkylamino group, a $C_{2-8}$ dialkylamino group, a $C_{2-8}$ acylamino group, a $C_{2-8}$ acylamino group having one to three halogen atoms, a $C_{1-8}$ alkylsulfonylamino group, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, or sulfamoyl;

$R^{13}$ is hydrogen, a $C_{1-8}$ alkyl group, a $C_{2-8}$ alkenyl group, a $C_{1-8}$ alkyl group having one to three halogen atoms, or an aralkyl group consisting of a $C_{6-10}$ aryl moiety and a $C_{1-3}$ alkylene moiety;

$R^{14}$ is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, an aralkyl group consisting of a $C_{6-10}$ aryl moiety and a $C_{1-3}$ alkylene moiety, a $C_{1-8}$ alkyl group having hydroxyl, a halogen atom. hydroxyl, nitro, cyano, amino, a $C_{1-8}$ alkylamino group, a $C_{1-5}$ alkylamino group having one to five halogen atoms, a $C_{2-8}$ dialkylamino group, a $C_{2-8}$ acylamino group, a $C_{2-8}$ acylamino group having one to three halogen atoms, a $C_{1-8}$ alkylsulfonylamino group, benzenesulfonylamino optionally having one or more substituents, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, sulfamoyl, phenyl optionally having one or more substituents, or a heterocyclic group optionally having one or more substituents; and the ring shown below is naphthalene ring, tetrahydronaphthalene ring, or indan ring.

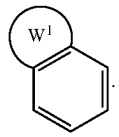

10. A compound or a pharmacologically acceptable salt thereof defined in claim 9, wherein each of $R^{11}$ and $R^{12}$ independently is hydrogen, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, or amino.

11. A compound or a pharmacologically acceptable salt thereof defined in claim 9, wherein $R^{13}$ is hydrogen or a $C_{1-8}$ alkyl group.

12. A compound or a pharmacologically acceptable salt thereof defined in claim 9, wherein $R^{14}$ is hydrogen, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a $C_{1-8}$ alkyl group having hydroxyl, a halogen atom, hydroxyl, cyano, amino, a $C_{1-8}$ alkylamino group, a $C_{2-8}$ dialkylamino group, a $C_{1-8}$ alkylsulfonylamino group, benzenesulfonylamino optionally having one or more substituents, phenyl optionally having one or more substituents, or a heterocyclic group optionally having one or more substituents.

13. A compound or a pharmacologically acceptable salt thereof defined in claim 9, wherein $R^{14}$ is a heterocyclic group optionally having one or more substituents, said heterocyclic group being tetrazolyl, triazolyl, pyridyl, imidazolyl, oxazolyl, or thiazolyl, and said substituents being selected from the group consisting of a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, and a $C_{2-8}$ dialkylamino group.

14. A compound or a pharmacologically acceptable salt thereof defined in claim 9, wherein $R^{14}$ is hydrogen, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, cyano, amino, a $C_{1-8}$ alkylamino group, a $C_{2-8}$ dialkylamino group, or benzenesulfonylamino optionally having one or more substituents, said substituents being selected from the group consisting of a $C_{1-8}$ alkyl group, a $C_{1-8}$ alkoxy group, a halogen atom, and nitro.

15. A compound or a pharmacologically acceptable salt thereof defined in claim 9, wherein the ring shown below is naphthalene ring.

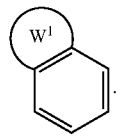

16. A compound having the formula (II) shown in claim 9, or a pharmacologically acceptable salt thereof, wherein $R^{11}$, $R^{12}$, $R^{13}$, and the ring shown below are the same as those defined in claim 9, and $R^{14}$ is $NHSO_2R$, wherein R is an aryl group optionally having one or more substituents or a heterocyclic group optionally having one or more substituents.

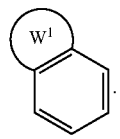

17. A compound or a pharmacologically acceptable salt thereof defined in claim 16, wherein R is phenyl, naphthyl, quinolyl, pyridyl, or thienyl, each of which optionally has one or more substituents selected from the group consisting of a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, hydroxyl, amino, nitro, and a halogen atom.

18. A $P2X_4$ receptor antagonist containing a compound or a pharmacologically acceptable salt thereof defined in claim 1 as an active ingredient.

19. A $P2X_4$ receptor antagonist containing a compound or a pharmacologically acceptable salt thereof defined in claim 9, as an active ingredient.

20. A therapeutic agent for neuropathic pain containing a compound or a pharmacologically acceptable salt thereof defined in claim 1, as an active ingredient.

21. A or therapeutic agent for neuropathic pain containing a compound or a pharmacologically acceptable salt thereof defined in claim 9, as an active ingredient.

\* \* \* \* \*